(12) United States Patent
Morikawa et al.

(10) Patent No.: US 10,288,564 B2
(45) Date of Patent: May 14, 2019

(54) REFLECTION CHARACTERISTIC MEASUREMENT SYSTEM

(71) Applicant: KONICA MINOLTA, INC., Chiyoda-ku (JP)

(72) Inventors: Takuma Morikawa, Sennan (JP); Yasutaka Tanimura, Nara (JP); Yasushi Goto, Sakai (JP); Yusaku Kawahara, Osaka (JP); Shinji Yamamoto, Sakai (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/950,902

(22) Filed: Apr. 11, 2018

(65) Prior Publication Data
US 2018/0299378 A1 Oct. 18, 2018

(51) Int. Cl.
| | | |
|---|---|---|
| *G01N 21/55* | (2014.01) | |
| *G01N 21/57* | (2006.01) | |
| *G01J 3/02* | (2006.01) | |
| *G01J 3/50* | (2006.01) | |
| *G01N 21/25* | (2006.01) | |
| *G01N 21/27* | (2006.01) | |
| *G01N 21/59* | (2006.01) | |
| *G01J 3/28* | (2006.01) | |

(52) U.S. Cl.
CPC ............ *G01N 21/57* (2013.01); *G01J 3/0272* (2013.01); *G01J 3/50* (2013.01); *G01N 21/251* (2013.01); *G01N 21/274* (2013.01); *G01N 21/5911* (2013.01); *G01J 2003/2866* (2013.01); *G01N 21/278* (2013.01)

(58) Field of Classification Search
CPC ........ G01J 3/0272; G01J 3/524; G01J 3/0291; G01J 3/46; G01N 21/251; G01N 21/274; G01N 21/57; G01N 21/5907; G01N 21/86
USPC .................. 356/600, 402, 407, 72, 445–448; 235/462.13, 462.04, 494, 462.49, 472.03
See application file for complete search history.

(56) References Cited

U.S. PATENT DOCUMENTS

| | | | | |
|---|---|---|---|---|
| 5,701,175 A | * | 12/1997 | Kostizak | ................... G01J 3/02 356/326 |
| 5,986,769 A | * | 11/1999 | Krzyminski | .............. G01J 3/50 356/445 |

(Continued)

*Primary Examiner* — Hoa Q Pham
(74) *Attorney, Agent, or Firm* — Cozen O'Connor

(57) ABSTRACT

A reflection characteristic measurement system includes: a hand-held reflection characteristic measurement apparatus including a light receiver that receives reflected light; and a guide member that supports the reflection characteristic measurement apparatus, wherein the guide member includes: a plate-shaped support part having a support surface to support the reflection characteristic measurement apparatus; and a white calibration plate applicable to white calibration of the reflection characteristic measurement apparatus, the support part includes: an elongated hole extending in one direction along the support surface; and a guide structure provided to guide the reflection characteristic measurement apparatus so as to enable the apparatus to move along the one direction, the light receiver is provided on the reflection characteristic measurement apparatus so as to move along a predetermined moving path, the moving path of the light receiver extends in the one direction, and the white calibration plate is provided on the moving path.

13 Claims, 16 Drawing Sheets

(56) References Cited

U.S. PATENT DOCUMENTS

| | | | | |
|---|---|---|---|---|
| 6,825,919 B2* | 11/2004 | Beimers | ................... | G01J 3/02 |
| | | | | 235/462.13 |
| 7,466,416 B2 | 12/2008 | Baker et al. | | |
| 8,422,017 B2* | 4/2013 | Gottwals | ............. | B41F 33/0036 |
| | | | | 356/402 |
| 2005/0068520 A1* | 3/2005 | Beimers | ................... | G01J 3/02 |
| | | | | 356/72 |

* cited by examiner

REFLECTION CHARACTERISTIC MEASUREMENT SYSTEM

The entire disclosure of Japanese patent Application No. 2017-078966, filed on Apr. 12, 2017, is incorporated herein by reference in its entirety.

BACKGROUND

Technological Field

The present invention relates to a technique for performing white calibration of a reflection characteristic measurement apparatus.

Description of the Related Art

There is a known reflection characteristic measurement apparatuses that measures reflected light obtained by emitting light to a measurement target to measure a reflection characteristic of the measurement target.

By using such a reflection characteristic measurement apparatus, for example, it is possible to perform a spot measurement of measuring the reflection characteristic of a measurement target in a minute region by immobilizing the reflection characteristic measurement apparatus and a scan measurement of continuously measuring the reflection characteristic of the measurement target by moving reflection characteristic measurement apparatus.

U.S. Pat. No. 7,466,416 discloses an apparatus using a plate-shaped guide member mounted on a color target as a reflection characteristic measurement apparatus used for scan measurement. The guide member includes an elongated hole extending in one direction parallel to the color target and a rail for moving the apparatus along the elongated hole. In a process of moving along the elongated hole, the apparatus measures the color target through the elongated hole.

Generally, in the inspection of the surface color of an industrial product, measurement of the reflection characteristic of a sample to be inspected (also referred to as a "measurement target") is greatly influenced by the geometry (optical conditions) of an illumination system and a light receiving system. Therefore, most reflection characteristic measurement apparatuses such as spectrocolorimeters employ any of geometry systems of 45/0 (45° illumination, vertical reception), 0/45 (vertical illumination, 45° reception) recommended by Commission internationale de l'éclairage (CIE), or any of d/0 (diffuse illumination, vertical reception), 0/d (vertical illumination, diffuse reception).

Typically, this type of reflection characteristic measurement apparatus stores a result of performing, in the same geometry as in the measurement of a sample, measurement of a white calibration plate with a known reflection characteristic as calibration data, and uses the calibration data, measurement results of the sample, and the known reflection characteristic of the white calibration plate to calculate the reflection characteristic of the sample. Operation of obtaining this calibration data is also referred to as white calibration.

As long as measurement characteristics of the reflection characteristic measurement apparatus such as the geometry, the light emission characteristic of a light source of an illumination system, and a photoelectric conversion characteristic of a light receiving system are maintained under same conditions, there would be not need to perform white calibration every time the sample is measured, and the same calibration data can be used in determination of the reflection characteristics.

In a case where the measurement characteristic of the reflection characteristic measurement apparatus changes due to aging, thermal change, or the like, however, the measurement condition for measuring the white calibration plate and the measurement condition for measuring the sample would not be the same measurement condition. Accordingly, there is a need to perform white calibration again by using a reflection characteristic measurement apparatus with the changed measurement characteristic.

Regarding the change in the measurement characteristic of the reflection characteristic measurement apparatus, the more the frequency of white calibration, the more accurately the change in the measurement characteristic of the reflection characteristic measurement apparatus can be corrected. In this, however, every time white calibration is performed, there is a need to install a white calibration plate in a measurement part of the reflection characteristic measurement apparatus and measure the white calibration plate. Accordingly, an increase in the frequency of white calibration increases a burden on the measurer.

A guide member disclosed in the specification of U.S. Pat. No. 7,466,416 includes a white calibration plate at a position different from a position on an axis of the elongated hole and includes a positioning projection to assist positioning of the reflection characteristic measurement apparatus to the measurement position of the white calibration plate. The measurer installs the reflection characteristic measurement apparatus on the positioning projection to allow the apparatus to be arranged at the measurement position of the white calibration plate. With this configuration, the technique of U.S. Pat. No. 7,466,416 attempts to reduce the burden on the measurer in white calibration of the reflection characteristic measurement apparatus used for scan measurement.

Unfortunately, however, when white calibration of the reflection characteristic measurement apparatus is performed using the technique described in the specification of U.S. Pat. No. 7,466,416, the measurer needs to lift the apparatus from a rail to guide the apparatus to a scan measurement path of the color target and move the apparatus to a part above the positioning member for white calibration and install the apparatus on the positioning member. This is a problem of the technique of the specification of U.S. Pat. No. 7,466,416 that the moving operation of the apparatus at the time of white calibration increases the load on the measurer.

SUMMARY

The present invention has been made to solve this problem, and an object thereof is to provide a technique capable of reducing the burden on a measurer at the time of white calibration of a reflection characteristic measurement apparatus used for scan measurement.

To achieve the abovementioned object, according to an aspect of the present invention, a reflection characteristic measurement system reflecting one aspect of the present invention comprises: a hand-held reflection characteristic measurement apparatus including, on a bottom part, a light receiver that receives reflected light obtained by emitting illumination light to a measurement target; and a guide member that supports the reflection characteristic measurement apparatus in a state of covering the measurement target so as to allow the light receiver to face the measurement target, wherein the guide member includes: a plate-shaped support part having a support surface to support the reflection characteristic measurement apparatus so as to enable the reflection characteristic measurement apparatus to move; and a white calibration plate provided on the guide member and applicable to white calibration of the reflection characteristic measurement apparatus, the support part includes: an elongated hole extending in one direction along the support surface to penetrate through the support part; and a guide structure provided to guide the reflection characteristic measurement apparatus so as to enable the apparatus to move along the one direction while being supported by the supporting surface, the light receiver is provided on the reflection characteristic measurement apparatus so as to move along a predetermined moving path by movement of the reflection characteristic measurement apparatus guided by the guide structure, the moving path of the light receiver extends in the one direction including a path of the light receiver to move in the one direction while facing the elongated hole, and the white calibration plate is provided on the moving path in plan view of the support part such that the light receiver faces a measurement surface of the white calibration plate when the light receiver moves along a part of the moving path.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

Embodiments

While the present invention is applicable to a reflection characteristic measurement apparatus without a spectroscopic element, the following description uses a spectroscopic reflection characteristic measurement apparatus as an example of a reflection characteristic measurement apparatus, and uses a spectral reflectance coefficient as a reflection characteristic to be measured by the reflection characteristic measurement apparatus as an example. In addition, description of an internal configuration of the reflection characteristic measurement apparatus will be omitted in the description of the cross-sectional views.

<White Calibration Plate>

In the present invention, a calibration reference plate to be measured with the same geometry as the measurement target and having a known reflection characteristic as a reference for obtaining a reflection characteristic of a measurement target is referred to as a white calibration plate.

1. First Embodiment

<Overview>

Figure 1:
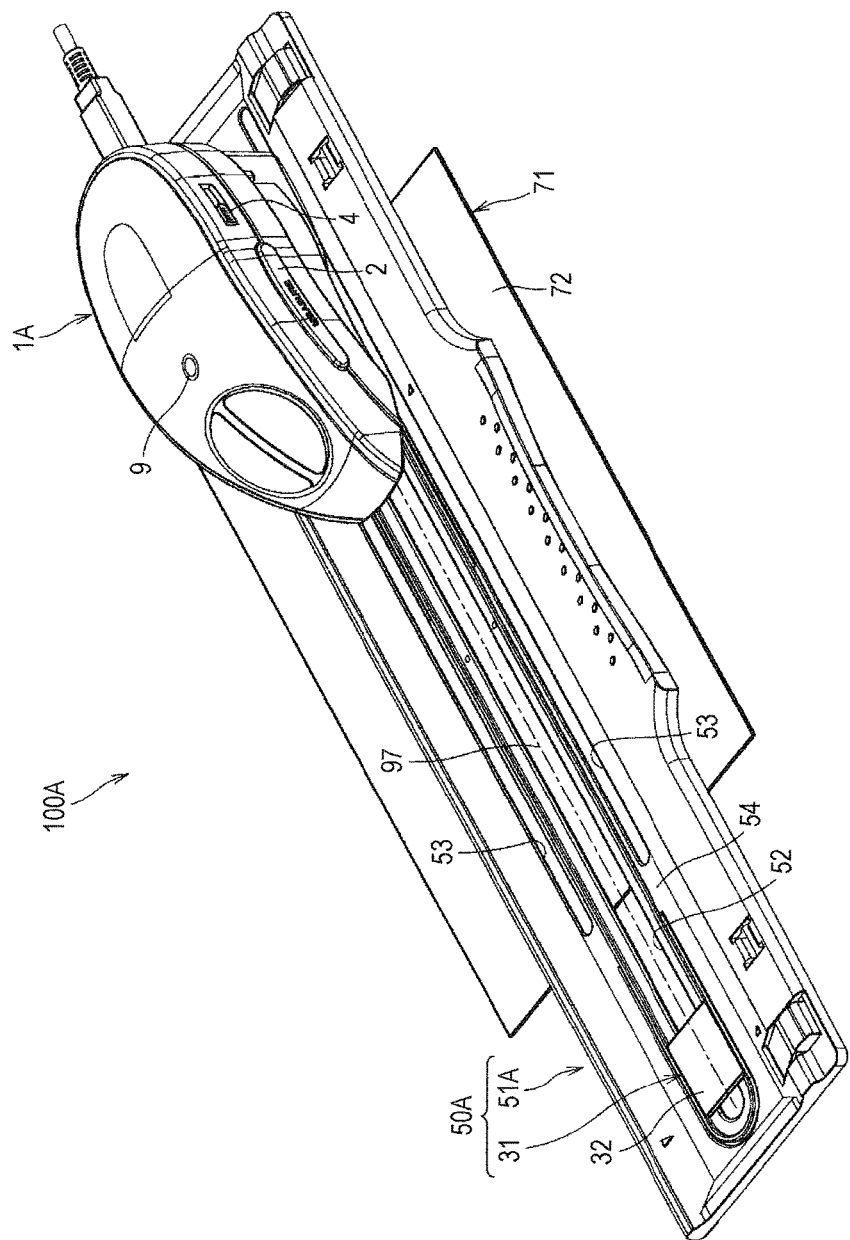
FIG. 1 is a perspective view illustrating a configuration of a reflection characteristic measurement system according to a first embodiment.
Figure 2:
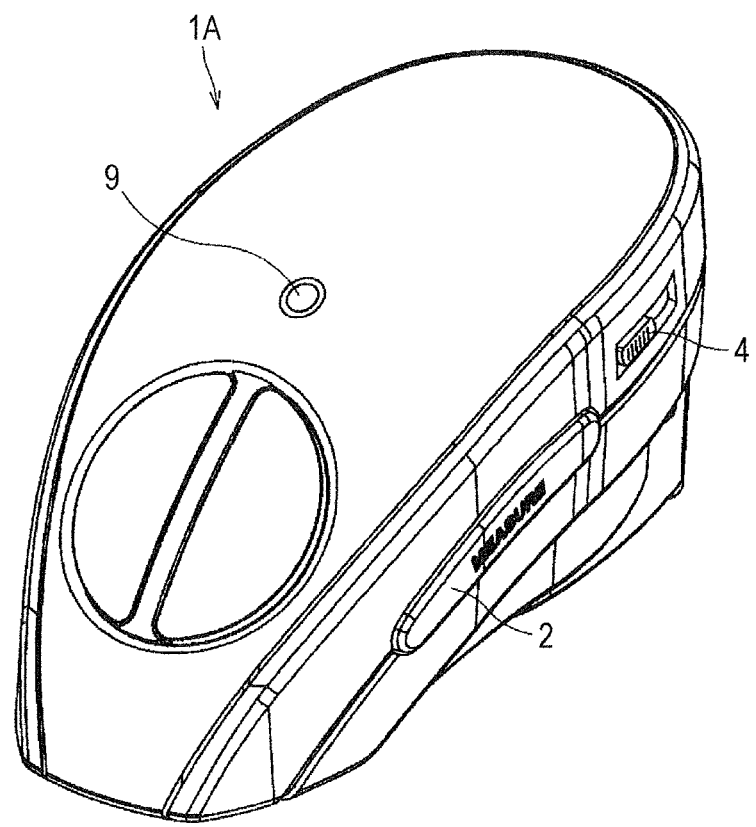
FIG. 2 is a perspective view illustrating an appearance of a top surface of a reflection characteristic measurement apparatus included in the system of FIG. 1.
Figure 3:
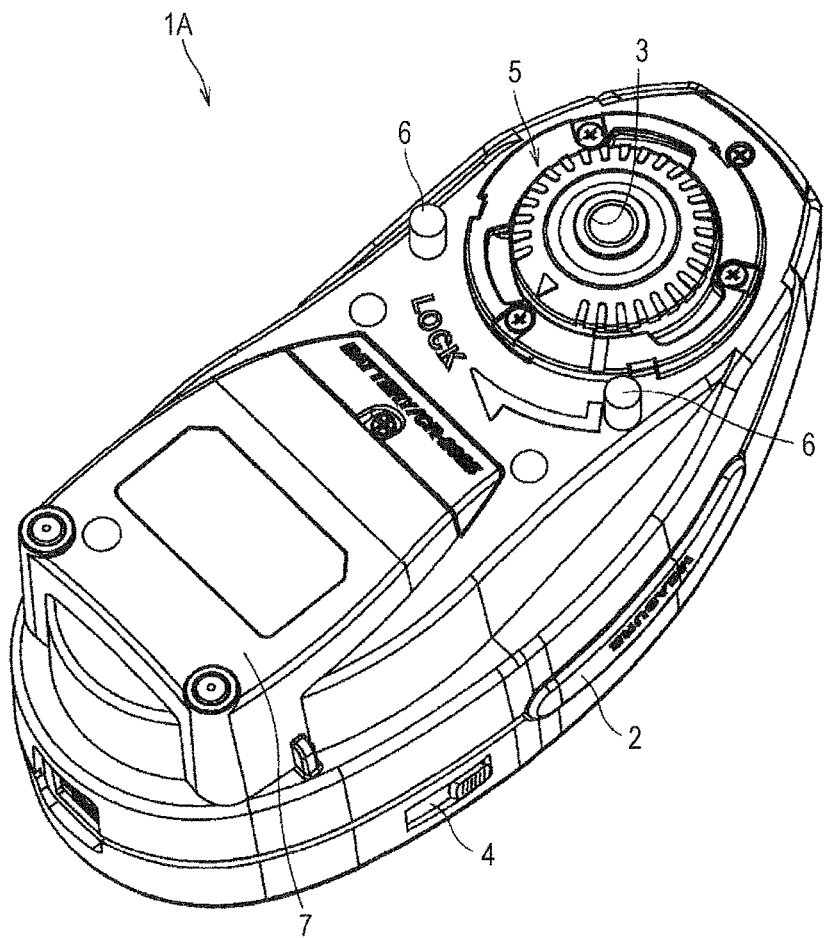
FIG. 3 is a perspective view illustrating an appearance of a lower surface of the reflection characteristic measurement apparatus of FIG. 2.

FIG. 1 is a perspective view illustrating a configuration of a reflection characteristic measurement system 100A according to a first embodiment. FIG. 2 is a perspective view illustrating an appearance of an upper surface of a reflection characteristic measurement apparatus 1A included in the reflection characteristic measurement system 100A. FIG. 3 is a perspective view illustrating an appearance of a lower surface of the reflection characteristic measurement apparatus 1A.

Figure 4:
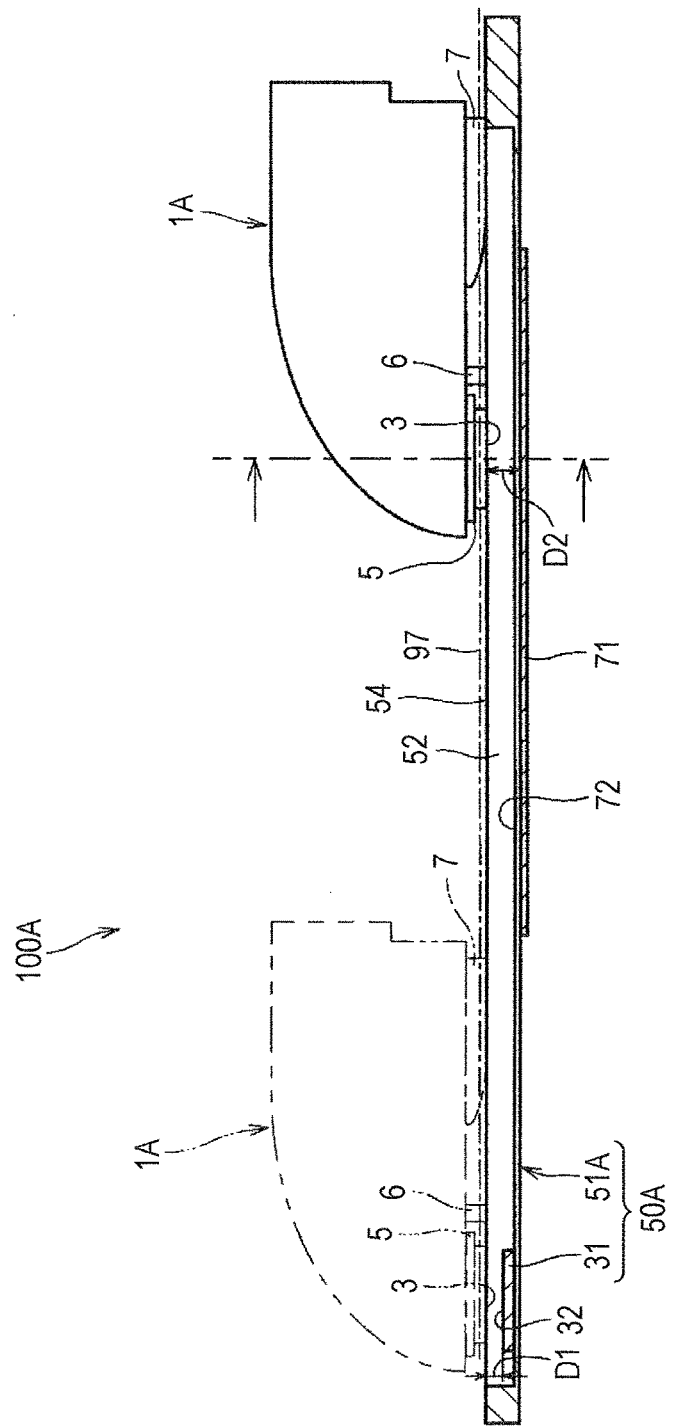
FIG. 4 is a schematic side sectional view illustrating a configuration of the reflection characteristic measurement system of FIG. 1.
Figure 5:
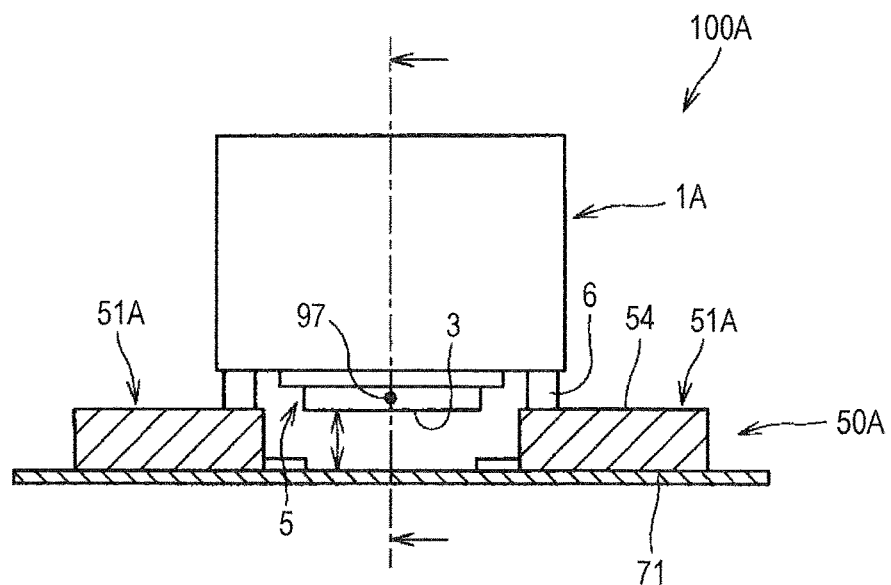
FIG. 5 is a schematic front sectional view of the reflection characteristic measurement system of FIG. 4.

FIG. 4 is a schematic side sectional view illustrating a configuration of the reflection characteristic measurement system 100A. FIG. 5 is a schematic front sectional view illustrating a configuration of the reflection characteristic measurement system 100A. A vertical direction is a direction perpendicular to a support surface of a guide member when the reflection characteristic measurement apparatus is mounted on the guide member, with the reflection characteristic measurement apparatus being positioned above the guide member.

The reflection characteristic measurement apparatus 1A illustrated in FIGS. 2 and 3 has a function to receive reflected light obtained by emitting light to a measurement target (also referred to as "measured object" or simply "sample") so as to measure a reflection characteristic of the measurement target on the basis of the reflected light.

Incidentally, the reflection characteristic measurement apparatus 1A includes, for example, a spectrocolorimeter, a colorimeter, a gloss meter, and a densitometer. While the example in each of the drawings of the present application illustrates a color patch sheet 71 as a measurement target, another measurement target may be used in place of the color patch sheet 71.

Reflected light is received through a light receiving opening 3 provided in a bottom part of a lower surface side (refer to FIG. 3) of the reflection characteristic measurement apparatus 1A. That is, the reflected light reflected by the color patch sheet ("measurement target") 71 is guided from the light receiving opening 3 into the inside of the reflection characteristic measurement apparatus 1A and used for measurement of the reflection characteristic in the reflection characteristic measurement apparatus 1A. Since the reflected light is guided from the light receiving opening 3 to the inside of the reflection characteristic measurement apparatus 1A, the light receiving opening 3 forms an opening of a cylindrical part 5 protruding from the bottom part of the reflection characteristic measurement apparatus 1A. The light receiving opening 3 is also referred to as a "light receiver" and a "measurement opening" in the reflection characteristic measurement apparatus 1A. In this manner, the reflection characteristic measurement apparatus 1A is a hand-held reflection characteristic measurement apparatus including, on the bottom part, a light receiver to receive the reflected light obtained by emitting illumination light on the measurement target.

<Configuration of Reflection Characteristic Measurement Apparatus 1A>

Figure 6:
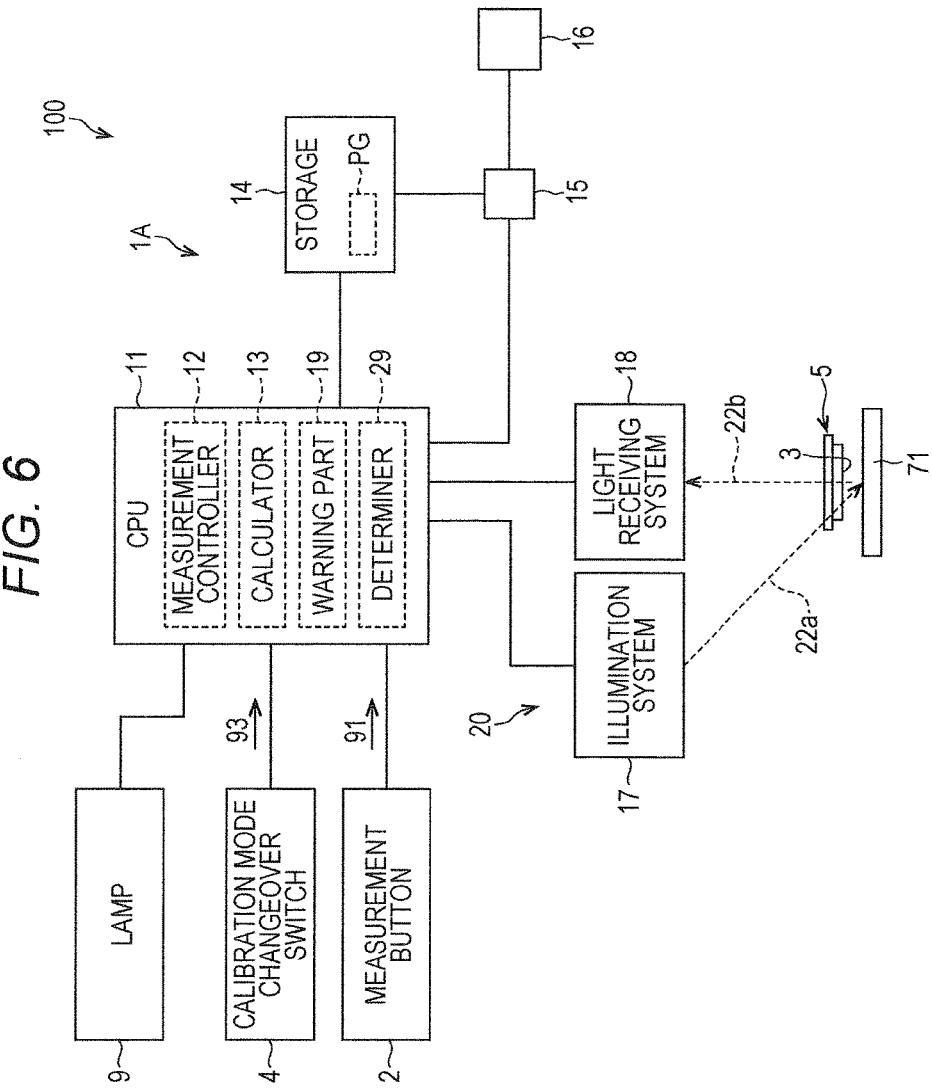
FIG. 6 is a schematic diagram illustrating a schematic configuration of the reflection characteristic measurement apparatus in FIG. 2.

FIG. 6 is a schematic diagram illustrating a schematic configuration of the reflection characteristic measurement apparatus 1A according to the first embodiment.

Operation of the reflection characteristic measurement apparatus 1A is controlled by a CPU 11 (also referred to as a "control processing unit"). The CPU 11 includes a temporary storage such as a RAM and is connected to a storage 14 as permanent information storage. The CPU 11 executes a program PG stored in the storage 14 so as to control operation of the reflection characteristic measurement apparatus 1A. Examples of the storage 14 include a flash memory and an EEPROM. The CPU 11 is also connected with various operation buttons and switches such as a measurement button 2 for instructing the reflection characteristic measurement apparatus 1A in white calibration operation and measurement operation, a calibration mode changeover switch 4 for switching a calibration mode described below, and a lamp 9 that blinks for warning is connected, enabling stand-alone operation of the reflection characteristic measurement apparatus 1A. The CPU 11 executes the program PG to also operate as a measurement controller 12, a calculator 13, a warning part 19, and a determiner 29 described below.

Each of the CPU 11 and the storage 14 is connected to a USB interface including a USB control circuit 15 and a USB connector 16. Through the USB interface, it is possible to control the reflection characteristic measurement apparatus 1A from an external apparatus such as a computer and perform bidirectional information transmission between the external apparatus and the reflection characteristic measurement apparatus 1A.

The reflection characteristic measurement apparatus 1A uses a main measurement system 20 (also referred to as an "illumination light receiver") to measure the reflection characteristic of the measurement target such as the color patch sheet 71 mounted to face the light receiving opening 3.

The main measurement system 20 includes: an illumination system 17 including a control circuit, a light source unit, and a lens (all not illustrated); and a light receiving system 18 including a lens, a polychromator having a spectroscopic element and a light receiving sensor array, and a processing circuit (all not illustrated).

The light source unit of the illumination system 17 uses a white light bulb, for example. The intensity of illumination light 22a output from the light source unit is adjusted by operating a control current supplied from the control circuit to the light source unit, by the CPU 11. Note that the illumination light 22a is representatively illustrated with one light beam to illustrate illumination light emitted on an entire surface of the light receiving opening 3 by a lens.

The lens of the light receiving system 18 allows diffusely reflected light 22b, that is, the illumination light 22a diffusely reflected from a surface of the measurement target, to be incident on the polychromator. The spectroscopic element spectrally decomposes the incident diffusely reflected light 22b in accordance with the wavelength and allows the light to be incident on the light receiving sensor array. An example of the spectroscopic element is a concave diffraction grating. Examples of the light receiving sensor array include a CCD sensor array and a CMOS array, used to photoelectrically convert incident light. The processing circuit reads electric charges converted by the light receiving sensor array, applies amplification processing, A/D conversion processing or the like, and outputs it to the CPU 11.

Moreover, various accessory components (accessory apparatuses) can be attached to this reflection characteristic measurement apparatus 1A. Specifically, as illustrated in FIGS. 1, 4, and 5, it is possible to attach a guide member (also referred to as a "scanning guide member") 50A to the reflection characteristic measurement apparatus 1A to perform scan measurement. The measurement information obtained by the reflection characteristic measurement apparatus 1A is transmitted to a personal computer (PC) (not illustrated) via a communication line. The reflection characteristic measurement apparatus 1A to which the accessory component is attached is also referred to as a reflection characteristic measurement system. The reflection characteristic measurement system 100A illustrated in FIG. 1 includes the reflection characteristic measurement apparatus 1A and the guide member 50A.

Hereinafter, a measurement method using the guide member 50A, that is, a measurement method using the reflection characteristic measurement system 100A will be described.

With the use of the guide member 50A, that is, in a case where the reflection characteristic measurement apparatus 1A is attached (mounted) on the guide member 50A as illustrated in FIG. 1, a measurer can perform scan measurement of continuously measuring a reflection characteristic of the color patch sheet 71 as the measurement target arranged along the moving path, while moving the reflection characteristic measurement apparatus 1A.

Figure 7:
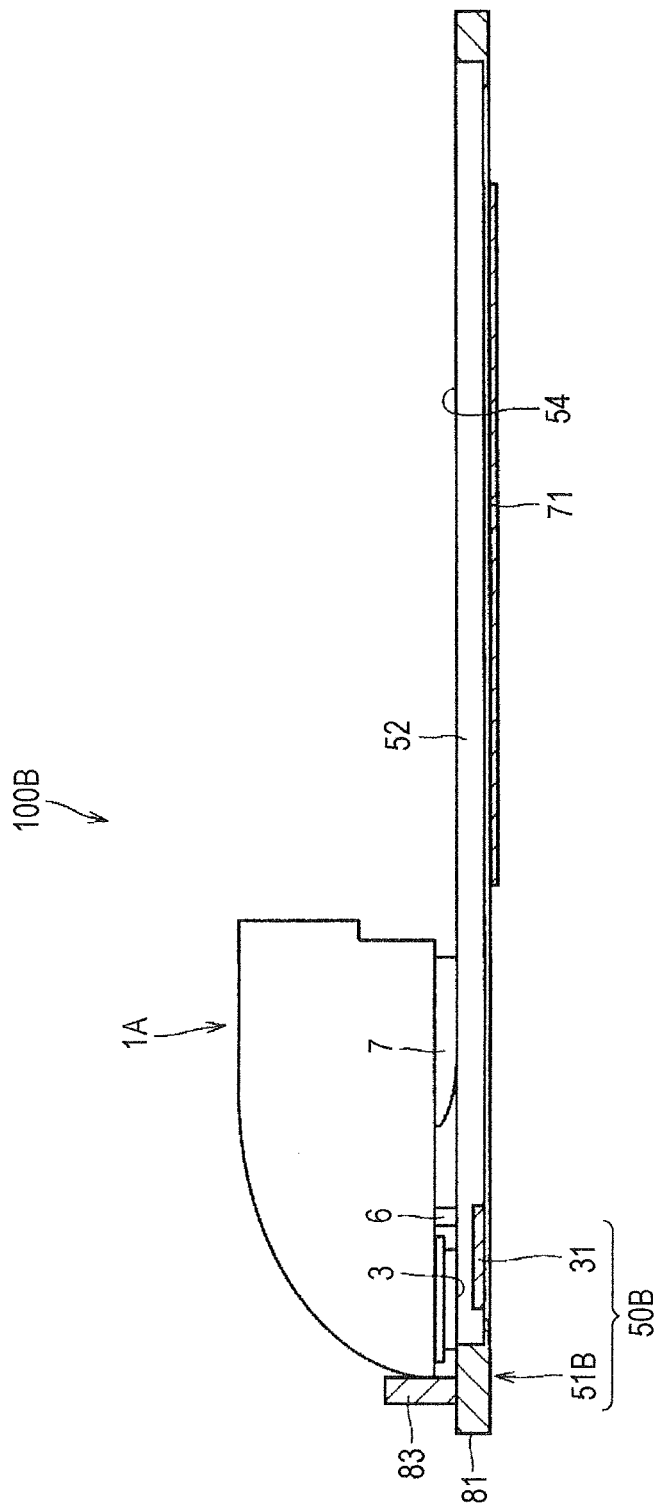
FIG. 7 is a schematic side sectional view illustrating a configuration of a reflection characteristic measurement system according to a second embodiment.

The guide member 50A includes a straight elongated hole 52 as illustrated in FIG. 7, for example. The guide member 50A is a member to support the reflection characteristic measurement apparatus 1A in a state of covering the measurement target so as to allow the light receiving opening 3 to face the measurement target.

The guide member 50A includes a plate-shaped support part 51A and a white calibration plate 31 used for white calibration of the reflection characteristic measurement apparatus 1A. The support part 51A has a support surface ("upper surface") 54 for supporting the reflection characteristic measurement apparatus 1A while allowing the reflection characteristic measurement apparatus 1A to move. The support surface 54 has a planar shape. The white calibration plate 31 is provided on the guide member 50A (support part 51A).

The support part 51A includes an elongated hole 52 and a guide groove 53. The elongated hole 52 extends in one direction along the support surface 54 and penetrates through the support part 51A in a direction penetrating the support surface 54. In a state where the reflection characteristic measurement apparatus 1A is mounted on the guide member 50A, the light receiving opening 3 of the reflection characteristic measurement apparatus 1A faces the elongated hole 52 of the guide member 50A. In addition, the reflection characteristic measurement apparatus 1A includes two protrusions 6 between the cylindrical part 5 of the bottom part on which the light receiving opening 3 is provided, and a bottom protrusion 7. In a state where the reflection characteristic measurement apparatus 1A is attached to the guide member 50A, each of the protrusions 6 is fitted into each of the guide grooves 53 of the guide member 50A. This makes it possible to linearly move the reflection characteristic measurement apparatus 1A along the guide groove 53, and the guide groove 53 guides the reflection characteristic measurement apparatus 1A so as to enable the reflection characteristic measurement apparatus 1A to be moved along the one direction (extending direction of the elongated hole 52) while being supported by the support surface 54. Note that the guide member 50A may include, instead of the guide groove 53, a rail part protruding from the support surface 54 to extend along the extending direction of the elongated hole 52 as a guide structure, and the reflection characteristic measurement apparatus 1A may include a groove part to be fixed in the rail part so as to enable the reflection characteristic measurement apparatus 1A to linearly move along the rail part.

The light receiving opening 3 is provided in the reflection characteristic measurement apparatus 1A so as to move along a predetermined moving path 97 with the movement of the reflection characteristic measurement apparatus 1A guided by the guide groove 53. The moving path 97 of the light receiving opening 3 extends in one direction including a path in which the light receiving opening 3 moves in the one direction (extending direction of the elongated hole 52) opposing the elongated hole 52. The white calibration plate 31 is provided on a part of the guide member 50A (support part 51A) on the moving path 97 in plan view of the support part 51A. When the light receiving opening 3 moves along a part of the moving path 97, the light receiving opening 3 faces a measurement surface ("upper surface") 32 of the white calibration plate 31. The measurement surface 32 is a flat surface. More specifically, the white calibration plate 31 illustrated in FIG. 1 is provided at a part on one end side of the guide member 50A (elongated hole 52). The surface to be measured is also referred to as a "measurement surface".

In actual scan measurement, the measurement button 2 is pressed while the reflection characteristic measurement apparatus 1A is moved. While the guide member 50A capable of linearly moving the reflection characteristic measurement apparatus 1A is illustrated here, the moving path (movement trajectory) of the reflection characteristic measurement apparatus 1A may be curved. In this case, the elongated hole 52 provided in the guide member 50A is curved along the moving path.

The determiner 29 determines whether the light receiving opening 3 faces the white calibration plate 31. The reflection characteristic measurement apparatus 1A can determine whether measurement for white calibration is available on the basis of the determination result by the determiner 29.

The intensity of the reflected light 22b received by the light receiving system 18 via the light receiving opening 3 during emission of the illumination light 22a by the illumination system 17 is high when the illumination light 22a is being emitted to the white calibration plate 31, while the intensity is low when the light is being emitted to the color patch sheet 71. Accordingly, the determiner 29 determines whether the light receiving opening 3 faces the white calibration plate 31 on the basis of the intensity of the reflected light 22b received by the light receiving system 18, that is, the intensity of the light received by the light receiving opening 3.

With the scan measurement performed using the guide member 50A in this manner, it is possible to suppress a displacement of the reflection characteristic measurement apparatus 1A with respect to the measurement target occurring in the movement of the reflection characteristic measurement apparatus 1A. Moreover, the present embodiment uses a configuration in which the reflection characteristic measurement apparatus 1A is attached to the guide member 50A so as to allow the moving direction of the reflection characteristic measurement apparatus 1A at the time of scan measurement to match the longitudinal direction of the reflection characteristic measurement apparatus 1A.

With this configuration, as compared with the guide member 50A to which the reflection characteristic measurement apparatus 1A can be attached to allow the moving direction of the reflection characteristic measurement apparatus 1A to be perpendicular to the longitudinal direction of the reflection characteristic measurement apparatus 1A at the time of scan measurement, it is possible to reduce an inclination occurring in the reflection characteristic measurement apparatus 1A at movement of the reflection characteristic measurement apparatus 1A, leading to stabilized movement operation of the reflection characteristic measurement apparatus 1A at the scan measurement.

Note that a white calibration distance D1 illustrated in FIG. 4 is a distance from the light receiving opening 3 of the reflection characteristic measurement apparatus 1A supported by the support part 51A of the guide member 50A, to the white calibration plate 31. A measurement distance D2 is a distance from the light receiving opening 3 of the reflection characteristic measurement apparatus 1A supported by the support part 51A to the color patch sheet 71 that is covered by the guide member 50A and faces the elongated hole 52.

In the guide member 50A, each of flange parts extending in the extending direction of the elongated hole 52 from each of both side walls of the elongated hole 52 formed in the support part 51A projects toward a center side of the elongated hole 52. The white calibration plate 31 is attached to both flange parts projecting from both side walls by bonding, or the like. This makes the measurement surface 32 of the white calibration plate 31 to be closer to the light receiving opening 3 compared with the measurement surface 72 of the color patch sheet 71. In other words, the white calibration plate 31 is provided on the guide member 50A such that the white calibration distance D1 differs from the measurement distance D2, more specifically, such that the white calibration distance D1 is shorter than the measurement distance D2. Even when the white calibration plate 31 is sandwiched between both side walls of the elongated hole 52, for example, without interposing the flange part, the white calibration distance D1 and the measurement distance D2 are usually different from each other due to the thickness of the white calibration plate 31.

Even in a case where the white calibration distance D1 differs from the measurement distance D2, a spectral reflectance Rm(λ) of the color patch sheet 71 in which the distance from the light receiving opening 3 is the measurement distance D2 satisfies Formula (1).

Therefore, in order to reduce an error in calculation of the reflectance of the measurement target due to the difference between the white calibration distance D1 and the measurement distance D2 in the reflection characteristic measurement system 100A, the calculator 13 of the reflection characteristic measurement apparatus 1A calculates the spectral reflectance Rm(λ) of the color patch sheet 71 as a measurement target by Formula (1).

[Mathematical Formula 2]

$$Rm(\lambda) = Rw0(\lambda) \times Im(\lambda)/Iwc1(\lambda) \times Iwc2(\lambda)/Iwc3(\lambda) \quad (2)$$

where

Rm(λ) represents spectral reflectance of the measurement target, in which the distance from the light receiving opening is the measurement distance, Rw0(λ) represents valued spectral reflectance of the white calibration plate in which the distance from the light receiving opening is the measurement distance, Im(λ) represents reflected light intensity obtained by the reflection characteristic measurement apparatus by measurement of the reflected light from the white calibration plate in which the distance from the light receiving opening is the measurement distance, Iwc1(λ) represents reflected light intensity obtained by the reflection characteristic measurement apparatus by measurement of the reflected light from the white calibration plate in which the distance from the light receiving opening is the white calibration distance, Iwc2(λ) represents reflected light intensity preliminarily obtained by the reflection characteristic measurement apparatus by measurement of the reflected light from the white calibration plate in which the distance from the light receiving opening is the white calibration distance, and Iwc3(λ) represents reflected light intensity obtained at the measurement of Iwc2(λ) by the reflection characteristic measurement apparatus by measurement of the reflected light from the white calibration plate in which the distance from the light receiving opening is the measurement distance.

That is, the calculator 13 calculates the spectral reflectance Rm(λ) of the color patch sheet 71 (measurement target) that satisfies Formula (1). The preliminarily valued spectral reflectance Rw0(λ) of the white calibration plate 31 in which the distance from the light receiving opening 3 is the measurement distance D2 and the preliminarily measured reflected light intensities Iwc2(λ) and Iwc3(λ) of the white calibration plate 31 are stored in the storage 14.

It is preferable that the reflected light intensities Iwc2(λ) and Iwc3(λ) are measured using the reflection characteristic measurement apparatus 1A to be calibrated in a calibration process in a manufacturing process of the reflection characteristic measurement apparatus 1A. That is, the reflected light intensities Iwc2(λ) and Iwc3(λ) are preferably measured by the reflection characteristic measurement apparatus 1A having the same measurement characteristics under the same measurement environment. With the reflection characteristic measurement apparatus 1A being mounted on the guide member 50A, the distance from the light receiving opening 3 to the white calibration plate 31 is the white calibration distance D1. Therefore, in the measurement of the reflected light intensity Iwc3(λ), a tool is used to set the distance from the light receiving opening 3 to the white calibration plate 31 to the measurement distance D2.

Note that a value obtained by dividing an integrated value of the preliminarily valued spectrally reflectance Rw0(λ) of the white calibration plate 31 in which the distance from the light receiving opening 3 is the measurement distance D2 and the preliminarily measured reflected light intensity Iwc2(λ) of the white calibration plate 31, by the reflected light intensity Iwc3(λ) corresponds to the preliminarily valued spectral reflectance of the white calibration plate 31 in which the distance from the light receiving opening 3 is the white calibration distance D1. Accordingly, the spectral reflectance may be preliminarily valued and stored in the storage 14 and used for calculating the spectral reflectance Rm(λ) of the color patch sheet 71.

<Procedure of Scan Measurement by Reflection Characteristic Measurement System 100A>

Figure 15:
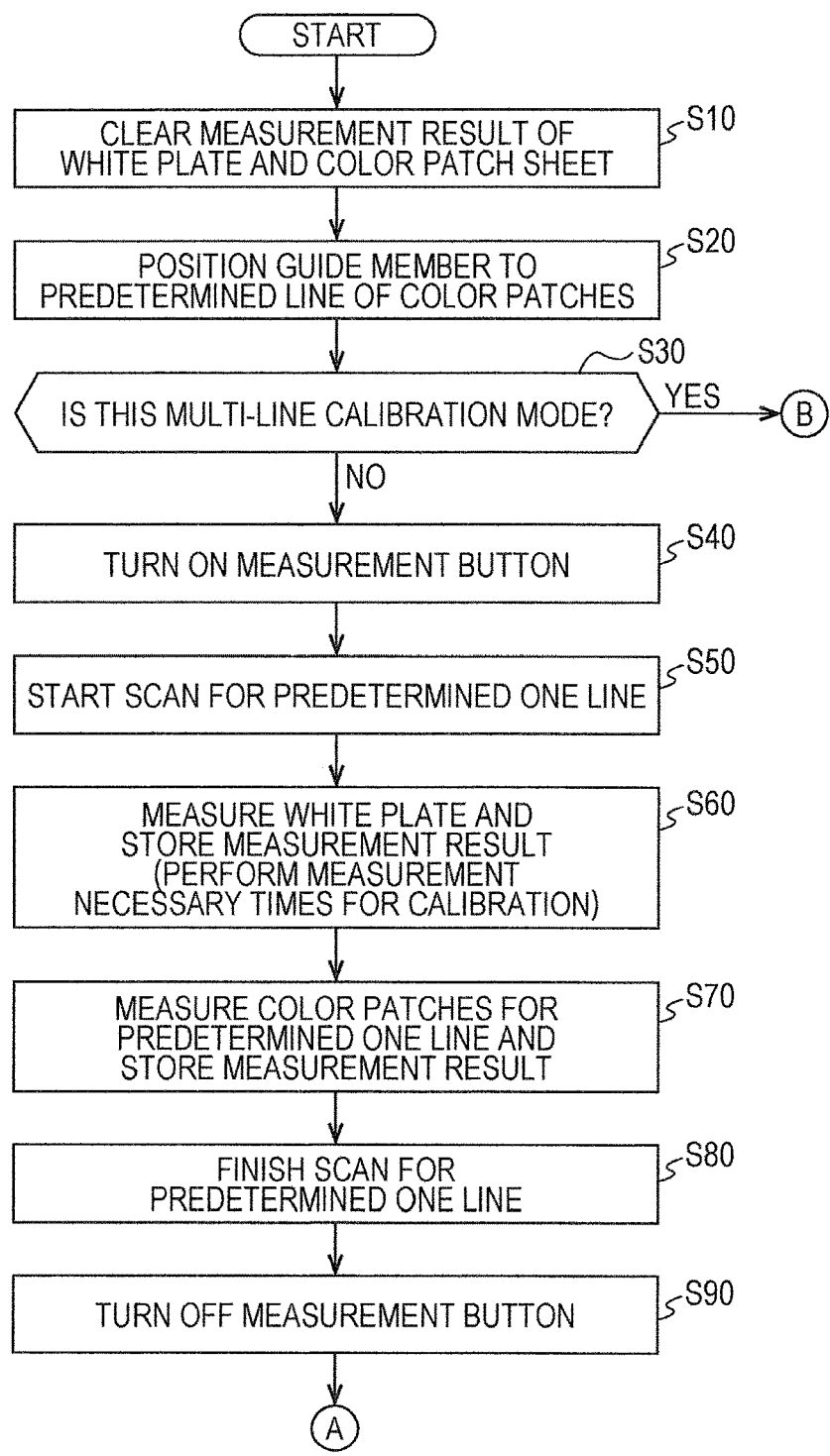
FIG. 15 is a flowchart illustrating a procedure of scan measurement.
Figure 16:
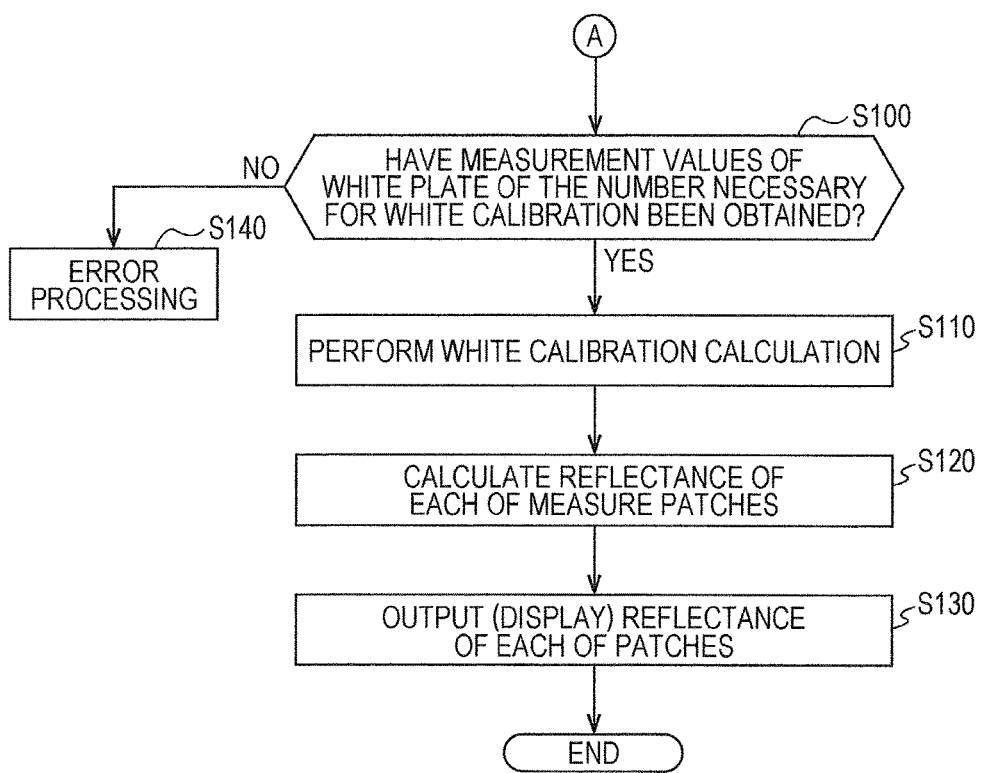
FIG. 16 is a flow chart illustrating a procedure of scan measurement.
Figure 17:
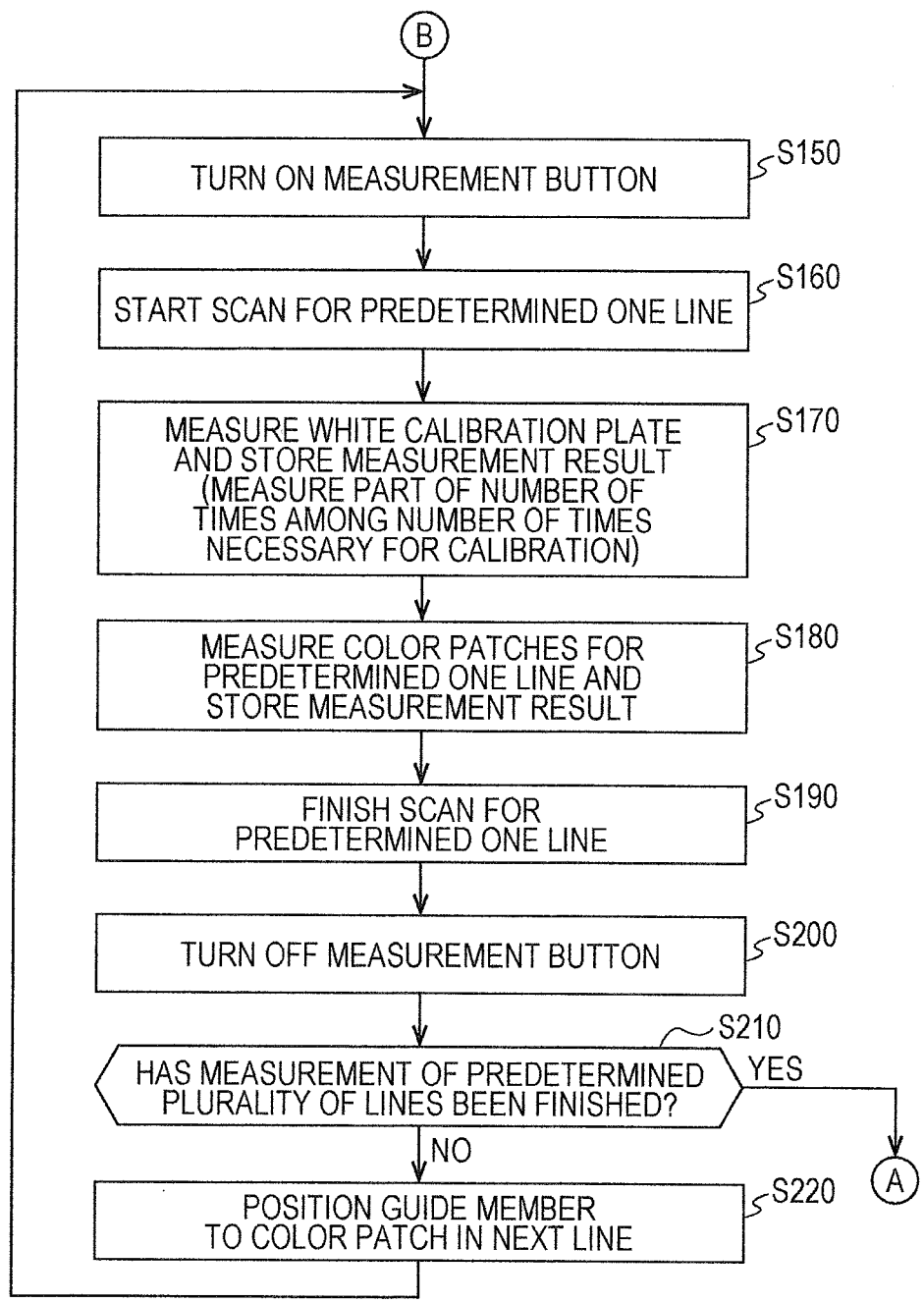
FIG. 17 is a flowchart illustrating a procedure of scan measurement.

Next, an operation process of performing scan measurement will be described. FIGS. 15 to 17 are flowcharts of operation (procedures) of scan measurement.

As illustrated in FIG. 15, in the case of performing the scan measurement, in step S10, for example, the start of power supply to the reflection characteristic measurement apparatus 1A by operation of a power button (not illustrated) of the reflection characteristic measurement apparatus 1A triggers the CPU 11 to clear a measurement result of each of the white calibration plate ("white plate") 31 and the color patch sheet 71 stored in the storage 14 of the reflection characteristic measurement apparatus 1A.

In step S20, the measurer positions the guide member 50A to the color patches in a predetermined line in the color patch sheet 71 in a state where the reflection characteristic measurement apparatus 1A is not attached to the guide member 50A.

Figure 10:
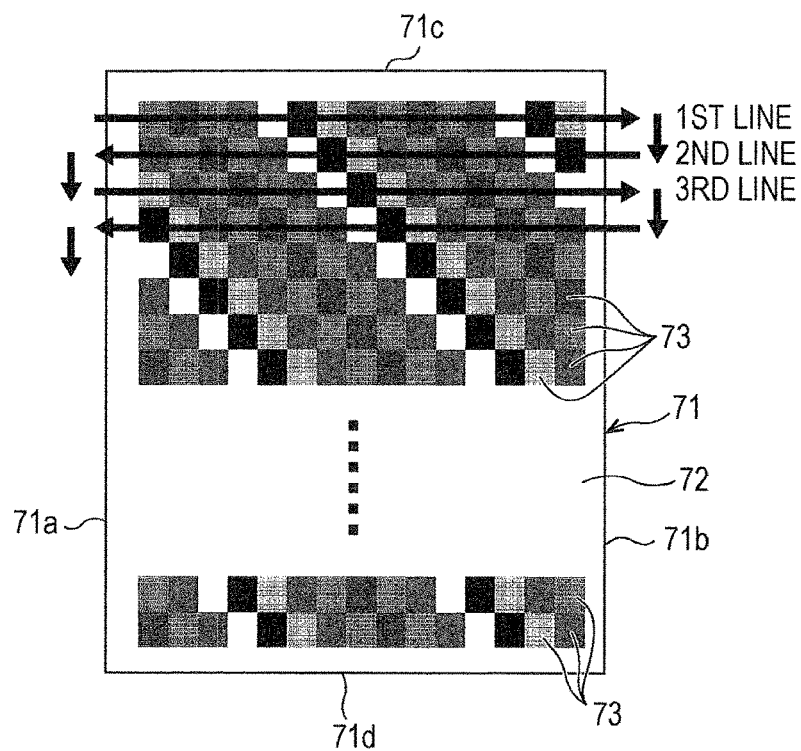
FIG. 10 is a plan view illustrating a schematic configuration of a color patch sheet.

FIG. 10 is a plan view illustrating an example of a schematic configuration of the color patch sheet 71. The shape of the color patch sheet 71 is, for example, a rectangle. The color patch sheet 71 is, for example, a sheet-like measurement target having a thickness of several tens μm to 1 mm. The measurement surface 72 of the color patch sheet 71 includes a plurality of color patch lines. Each of the color patch lines is formed by arranging a plurality of color patches in a line. The extending direction of each of the lines is a direction orthogonal to each of sides forming one end 71a and the other end 71b of the color patch sheet 71.

More specifically, the measurer arranges, in step S20, for example, the guide member 50A to allow the arrangement direction of the individual color patches in each of the color patch lines to match the extending direction of the elongated hole 52 on the color patch line in the first line (line closest to the upper end 71c of the color patch sheet 71) illustrated in FIG. 10 so as to position the elongated hole 52 on the color patch line. The measurer further mounts the reflection characteristic measurement apparatus 1A on the guide member 50A. For example, the guide member 50A is arranged to allow the white calibration plate 31 to be positioned on more left side (one end 71a side with respect to the other end 71b) than the color patch on the one end 71a side on a paper surface of FIG. 10.

Note that the calibration mode changeover switch 4 of the reflection characteristic measurement apparatus 1A is preset to one of a multi-line calibration mode and a single-line calibration mode by a measurer, and a calibration mode setting signal 93 is supplied from the calibration mode changeover switch 4 to the CPU 11.

In step S30 of FIG. 15, the measurement controller 12 determines whether the calibration mode is the multi-line calibration mode on the basis of the calibration mode setting signal 93.

In a case where it is determined that the calibration mode is not the multi-line calibration mode, that is, the mode is the single-line calibration mode, the measurement controller 12 of the CPU 11 performs single-line calibration control (first control) of controlling the reflection characteristic measurement apparatus 1A to perform a predetermined number of times of white calibration measurements necessary for white calibration within one input period of a measurement signal 91.

In step S40, the measurer presses the measurement button 2 to turn it on.

In step S50, the measurer starts scanning the color patch line on which the elongated hole 52 is mounted using the reflection characteristic measurement apparatus 1A.

The measurer arranges the reflection characteristic measurement apparatus 1A on the guide member 50A to set the light receiving opening 3 of the reflection characteristic measurement apparatus 1A to be positioned above the white calibration plate 31, and scans the reflection characteristic measurement apparatus 1A from the side of one end 71a toward the other end 71b side.

In step S60, the reflection characteristic measurement apparatus 1A measures the white calibration plate 31 (a predetermined number of times of measurements for white calibration necessary for white calibration) and stores a result of the measurement in the storage 14 in the process of scanning.

In step S70, the reflection characteristic measurement apparatus 1A measures individual color patches of the current color patch line and stores the measurement results in the storage 14.

In step S80, the measurer finishes the scanning of the one line.

In step S90, the measurer releases the measurement button to turn it off.

In step S100 of FIG. 16, the warning part 19 determines whether the number of the white calibration plate 31 measurement values necessary for white calibration has been obtained.

In a case where it is determined that the number of measurement values necessary for white calibration has not been obtained, the warning part 19 performs error processing of issuing a predetermined warning in step S140. An example of the error processing is processing by the warning part 19 to cause the lamp 9 provided on the upper surface of the reflection characteristic measurement apparatus 1A to blink. The warning part 19 (CPU 11) is capable of supplying a signal of controlling the turning-on and turning-off of the lamp 9, and also capable of causing the lamp 9 to blink.

In a case where it is determined in step S100 that the number of measurement values necessary for white calibration has been obtained, the calculator 13 executes in step S110 white calibration calculation of calculating a reflected light intensity Iwc1($\lambda$) of the white calibration plate 31 in which the distance from the light receiving opening 3 is the white calibration distance D1 on the basis of an average value of individual measurement values.

In step S120, the calculator 13 calculates the spectral reflectance Rm($\lambda$) on the basis of: reflected light intensity Im($\lambda$) measured in each of measured patches; the reflected light intensity Iwc1($\lambda$); the preliminarily valued spectral reflectance Rw0($\lambda$) of the white calibration plate 31 stored in the storage 14 in advance; the preliminarily measured reflected light intensity Iwc2($\lambda$) of the white calibration plate 31 at the white calibration distance D1; and the preliminarily measured reflected light intensity Iwc3($\lambda$) of the white calibration plate 31 at the measurement distance D2, by Formula (1).

In step S130, the CPU 11 outputs the spectral reflectance Rm($\lambda$) of each of the patches to a personal computer (PC) or the like, and the PC displays a measurement result on a monitor.

This completes the measurement of one line of color patches in the single-line calibration mode.

In a case where it is determined in step S30 that the calibration mode is the multi-line calibration mode, the measurement controller 12 of the CPU 11 performs multi-line calibration control (second control) of controlling the main measurement system 20 to perform a predetermined number of white calibration measurements by distributing the measurement to each of a plurality of number of times of input periods of the measurement signal 91.

In step S150 of FIG. 17, the measurer presses the measurement button 2 to turn it on.

In step S160, the measurer starts scanning the color patch line on which the elongated hole 52 is mounted by using the reflection characteristic measurement apparatus 1A.

The measurer arranges the reflection characteristic measurement apparatus 1A on the guide member 50A to set the light receiving opening 3 of the reflection characteristic measurement apparatus 1A to be positioned above the white calibration plate 31, and scans the reflection characteristic measurement apparatus 1A from the side of one end 71a toward the other end 71b side.

In step S170, the reflection characteristic measurement apparatus 1A measures the white calibration plate 31 (a part of the number of times among a predetermined number of times of measurements for white calibration necessary for white calibration) and stores a result of the measurement in the storage 14 in the process of scanning.

In step S180, the reflection characteristic measurement apparatus 1A measures individual color patches of the current color patch line and stores the measurement results in the storage 14.

In step S190, the measurer finishes the scanning of the one line.

In step S200, the measurer releases the measurement button to turn it off.

In step S210, the CPU 11 determines whether the measurement of a plurality of predetermined lines has been completed on the basis of the number of times of turning-on of the measurement button 2, or the like.

In a case where the measurement of the plurality of predetermined lines has not been completed, the CPU 11 notifies incompletion of the measurement to the measurer by lighting of the lamp 9 or the like, and prompts the measurer to retry the measurement.

In step S220, the measurer performs positioning of the guide member 50A to a color patch of the next line (next color patch line), more specifically, to a color patch in the line adjacent to the line in which the measurement is completed on the lower end 71d side of the color patch sheet 71.

Processing of step S150 to step S200 is performed similarly to the measurement of the immediately preceding line, and the determination of step S210 is performed again.

In a case where it is determined in S210 that the measurement of the plurality of predetermined lines has been completed, the warning part 19, the calculator 13, or the like, perform processing of steps S100 to S130 (S140) in FIG. 16 similarly to the case of the single-line calibration mode.

This completes the measurement of the plurality of predetermined lines of color patches in the multi-line calibration mode.

With reference to FIGS. 15 to 17, as described above, the measurement controller 12 detects the measurement signal 91 from the measurement button 2 input to the reflection characteristic measurement apparatus 1A, and controls the main measurement system 20 of the reflection characteristic measurement apparatus 1A to perform measurement for white calibration and measurement for the measurement target. More specifically, the measurement controller 12 selectively performs the first control of controlling the reflection characteristic measurement apparatus 1A to perform measurement for white calibration a predetermined number of times necessary for white calibration within one input period of the measurement signal 91, and the second control of controlling the main measurement system 20 to perform a predetermined number of white calibration measurements by distributing the measurement to each of a plurality of number of times of input periods of the measurement signal 91.

It is also allowable to configure such that the reflection characteristic measurement apparatus 1A has no calibration mode changeover switch 4, and that the measurement controller 12 is able to perform any one of the first control and the second control.

In the case of scanning a plurality of lines of color patches using the reflection characteristic measurement apparatus 1A, the measurer may scan, for each line, the reflection characteristic measurement apparatus 1A in a certain direction on the guide member 50A such that the reflection characteristic measurement apparatus 1A performs the measurement for white calibration and thereafter performs color patch measurement, as described in steps S170 and S180 of FIG. 17. Moreover, for example, as illustrated in FIG. 10, the measurer may move the reflection characteristic measurement apparatus 1A to alternately reverse the scanning direction for each of the lines to cause the reflection characteristic measurement apparatus 1A to change the order of execution of the measurement for white calibration and the measurement of the color patch in accordance with the scanning direction.

In a case where the execution order of the measurement for the white calibration plate 31 and for the color patch sheet 71 is changed in accordance with the scanning direction, the determiner 29 may determine whether the light receiving opening 3 faces the white calibration plate 31, and the measurement controller 12 may determine the execution order of individual measurements on the basis of the determination result. In addition, the measurement controller 12 may control the reflection characteristic measurement apparatus 1A to perform these measurements in accordance with the execution order of measurements over a plurality of preset lines in which the execution order of measurements alternates for each of the scans.

<White Calibration Plate 31>

Figure 11:
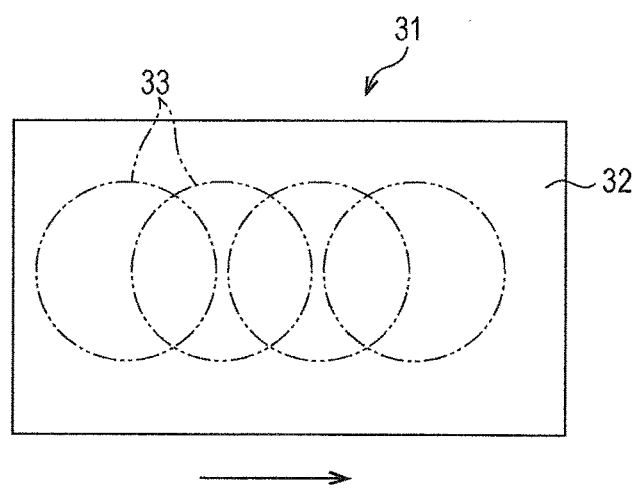
FIG. 11 is a schematic plan view illustrating a white calibration plate.

FIG. 11 is a schematic plan view illustrating the white calibration plate 31.

As illustrated in FIG. 11, the reflection characteristic measurement system 100A is configured such that the measurement surface 32 of the white calibration plate 31 is longer in one direction (extending direction of the elongated hole 52) along the measurement surface 32 than in a direction crossing the one direction. This makes it possible to make the white calibration plate 31 wider than a measurement diameter 33 of the main measurement system 20 and to allow the measurement surface 32 to include a plurality of measurement diameters 33 along the one direction, leading to enhancement of reliability of white calibration by increasing the number of times of measurement of the calibration plate 31.

2. Second Embodiment

FIG. 7 is a schematic side sectional view illustrating a configuration of a reflection characteristic measurement system 100B according to a second embodiment. As illustrated in FIG. 7, the reflection characteristic measurement system 100B is configured similarly to the reflection characteristic measurement system 100A except that a guide member 50B is provided in place of the guide member 50A of the reflection characteristic measurement system 100A.

In the reflection characteristic measurement system 100B, the white calibration plate 31 is provided on a part of the guide member 50B on one end 81 side in one direction. The support part 51B includes an abutment part 83 protruding from a part of the support surface 54 on the one end 81 side of the guide member 50B. The abutment part 83 is provided on the support part 51B such that the abutment part 83 abuts the reflection characteristic measurement apparatus 1A to enable regulation of the movement of the reflection characteristic measurement apparatus 1A toward the one end 81 side in a state where the light receiver faces a predetermined part of the measurement surface 32 of the white calibration plate 31. The support part 51B is configured similarly to the case of the support part 51A except that the abutment part 83 is provided.

This configuration enables the measurer to easily and more reliably position the light receiving opening 3 of the reflection characteristic measurement apparatus 1A with respect to the white calibration plate 31 by using the abutment part 83. It is preferable that the predetermined position on the white calibration plate 31 is set to a position at which the reflection characteristic measurement apparatus 1A can perform measurement of the number of times necessary for white calibration at a typical scanning speed, for example.

3. Third Embodiment

Figure 8:
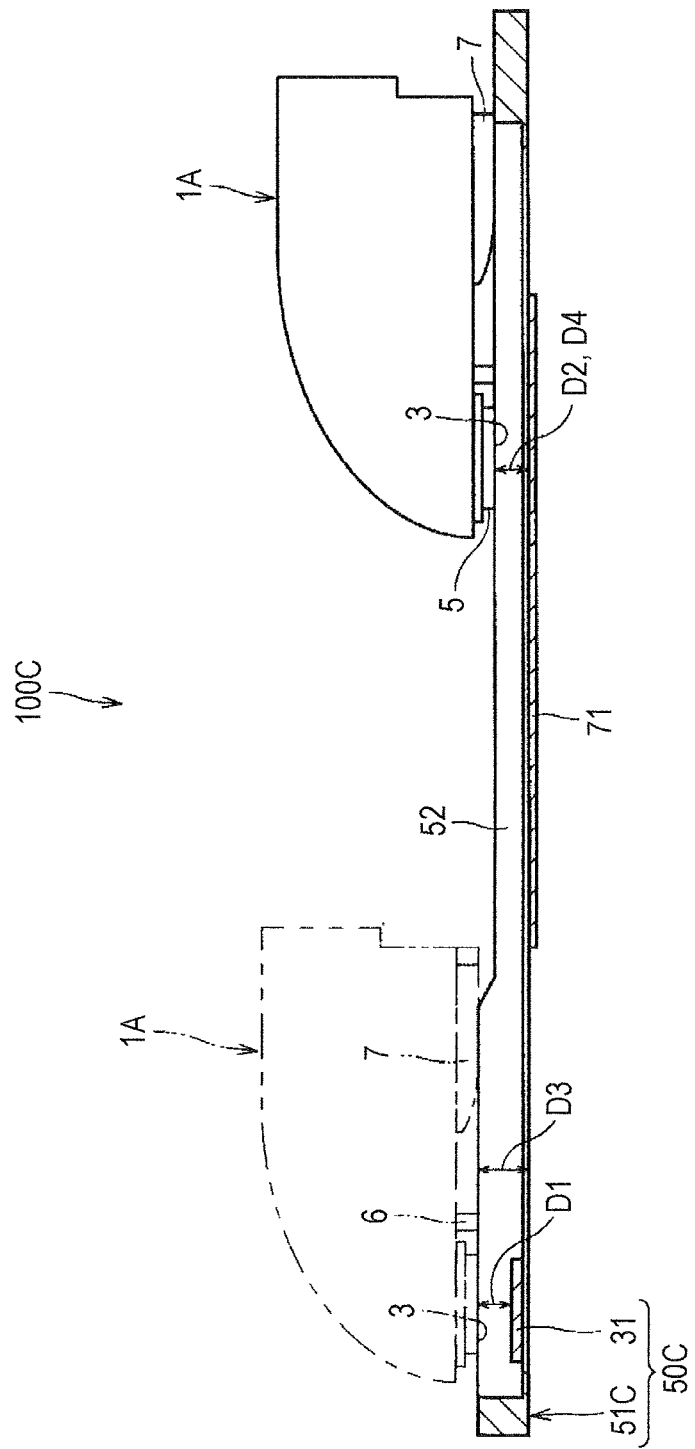
FIG. 8 is a schematic side sectional view illustrating a configuration of a reflection characteristic measurement system according to a third embodiment.

FIG. 8 is a schematic side sectional view illustrating a configuration of a reflection characteristic measurement system 100C according to a third embodiment. As illustrated in FIG. 8, the reflection characteristic measurement system 100C is configured similarly to the reflection characteristic measurement system 100A except that a guide member 50C is provided in place of the guide member 50A of the reflection characteristic measurement system 100A.

The guide member 50C is configured similarly to the guide member 50A, except that the support part 51C is provided in place of the support part 51A of the guide member 50A.

The white calibration distance D1 in the reflection characteristic measurement system 100C is a distance from the light receiving opening 3 of the reflection characteristic measurement apparatus 1A supported by the support part 51C of the guide member 50C, to the white calibration plate 31. The measurement distance D2 is a distance from the light receiving opening 3 of the reflection characteristic measurement apparatus 1A supported by the support part 51C to the color patch sheet 71 that is covered by the guide member 50C and faces the elongated hole 52.

Here, a first thickness D3 is defined by a thickness of a part, among the support part 51C, that supports the reflection characteristic measurement apparatus 1A so as to allow the light receiving opening 3 to face the white calibration plate 31. A second thickness D4 is defined by a thickness of a part, among the support part 51C, that supports the reflection characteristic measurement apparatus 1A so as to allow the light receiving opening 3 to face the color patch sheet 71. This leads to a configuration of the reflection characteristic measurement system 100C in which the first thickness D3 and the second thickness D4 are mutually different so as to equalize the white calibration distance D1 and the measurement distance D2. The support part 51C is configured similarly to the support part 51A except for the difference in thickness between the two parts.

Since the white calibration distance D1 and the measurement distance D2 are equalized, the white calibration plate 31 and the color patch sheet 71 can be measured with the same geometry, leading to enhancement of the measurement accuracy of the reflectance of the color patch sheet 71.

4. Fourth Embodiment

Figure 9:
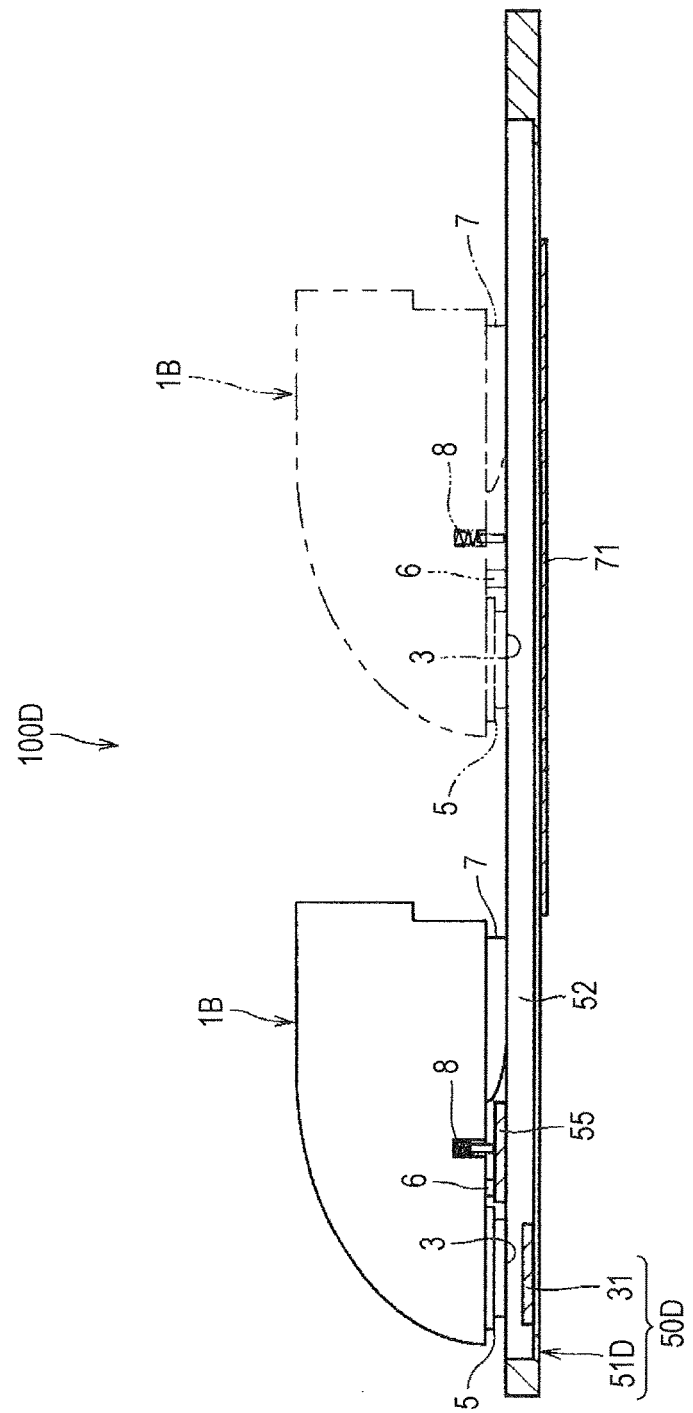
FIG. 9 is a schematic side sectional view illustrating a configuration of a reflection characteristic measurement system according to a fourth embodiment.

FIG. 9 is a schematic side sectional view illustrating a configuration of a reflection characteristic measurement system 100D according to a fourth embodiment. The reflection characteristic measurement system 100D is configured similarly to the measurement system 100A except that a guide member 50D is provided in place of the guide member 50A of the reflection characteristic measurement system 100A and a reflection characteristic measurement apparatus 1B is provided instead of the reflection characteristic measurement apparatus 1A.

The reflection characteristic measurement apparatus 1B is configured similarly to the reflection characteristic measurement apparatus 1A except that a sensor 8 not included in the reflection characteristic measurement apparatus 1A is provided and that the determiner 29 determines whether the light receiving opening 3 faces the white calibration plate 31 on the basis of a detection signal output from the sensor 8. The guide member 50D is configured similarly to the guide member 50A, except that the support part 51D is provided in place of the support part 51A of the guide member 50A.

In the reflection characteristic measurement system 100D, the support part 51D of the guide member 50D further includes a projection 55 ("identification mark") on its upper surface. The projection 55 is provided on a movement trajectory of the support part 51D in plan view with respect to the movement trajectory of the reflection characteristic measurement apparatus 1B supported by the support part 51D and guided by the guide groove 53. Moreover, the projection 55 has substantially the same length as the length of the white calibration plate 31 in one direction (extending direction of the elongated hole 52). The support part 51D is configured similarly to the support part 51A except that the projection 55 is provided.

The reflection characteristic measurement apparatus 1B further includes the sensor 8 that detects the projection 55 and outputs a predetermined detection signal. The sensor 8 includes a member biased toward the guide member 50D side by a spring and a switch to output a detection signal by contact of the member. When the member biased by the spring of the sensor 8 is not in contact with the projection 55, the member and the switch are not brought into contact. When the member comes into contact with the projection 55, the member is pushed upward to come in contact with the switch to cause the sensor 8 to output a detection signal. The sensor 8 is electrically connected to the CPU 11, and thus, the detection signal is supplied to the CPU 11.

The positional relationship of the sensor 8 with respect to the white calibration plate in one direction (extending direction of the elongated hole 52) of the projection 55 is substantially equal to the positional relationship of the sensor 8 with respect to the light receiving opening 3 of the reflection characteristic measurement apparatus 1B supported by the support part 51D in the one direction.

Accordingly, the light receiving opening 3 faces the white calibration plate 31 in a case where the sensor 8 outputs a detection signal. The determiner 29 (CPU 11) of the reflection characteristic measurement apparatus 1B can determine whether the light receiving opening 3 faces the white calibration plate 31 by detecting this detection signal, enabling the reflection characteristic measurement system 100B to enhance the accuracy of the execution timing of white calibration.

For example, it is allowable to use a magnet or the white calibration plate 31 itself and use a magnetic sensor, a camera, or the like, as the sensor 8 to detect the identification mark.

5. Fifth Embodiment

Figure 12:
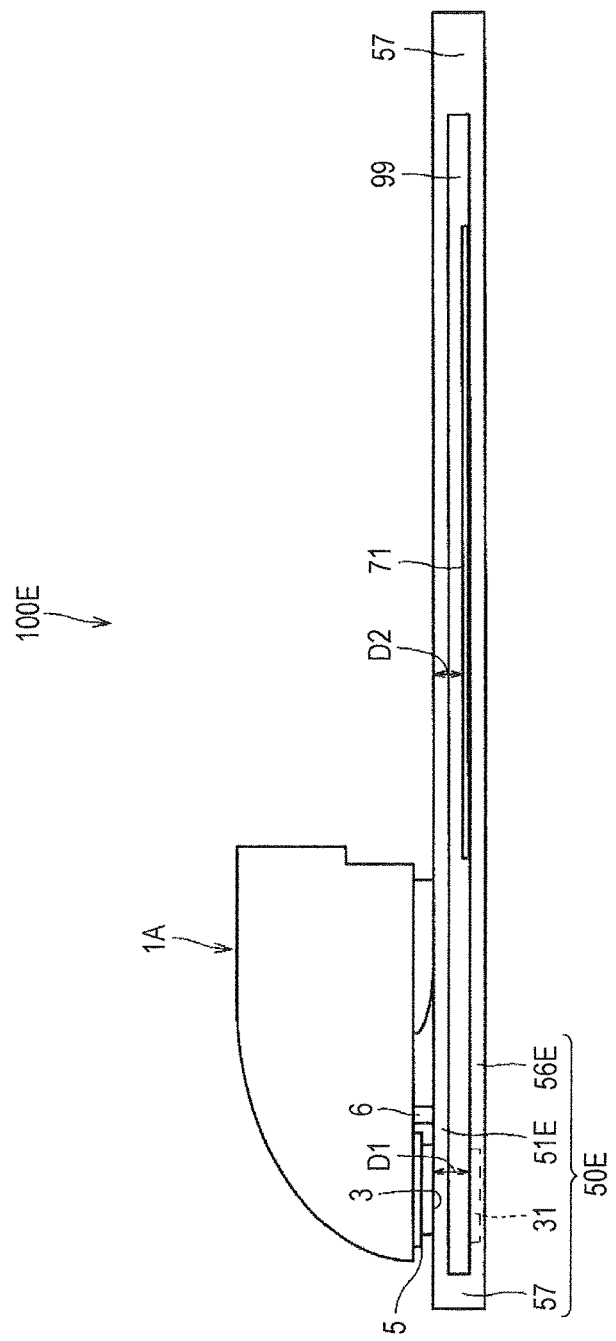
FIG. 12 is a schematic side sectional view illustrating a configuration of a reflection characteristic measurement system according to a fifth embodiment.

FIG. 12 is a schematic side sectional view illustrating a configuration of a reflection characteristic measurement system 100E according to a fifth embodiment.

The reflection characteristic measurement system 100E is configured similarly to the reflection characteristic measurement system 100A except that a guide member 50E is provided in place of the guide member 50A of the reflection characteristic measurement system 100A. The guide member 50E is configured similarly to the guide member 50A, except that the guide member 50E includes a support part 51E in place of the support part 51A of the guide member 50A, and further includes a facing part 56E and a connecting part 57.

The facing part 56E is a plate-shaped member facing the support part 51E and on which the white calibration plate 31 is provided. The connecting part 57 connects the support part 51E and the facing part 56E such that the support part 51E and the facing part 56E face each other across a predetermined gap 99 extending in one direction (extending direction of the elongated hole 52). The support part 51E is configured similarly to the support part 51A except that the white calibration plate 31 is not provided and that both end parts in the one direction are connected to the connecting part 57.

Therefore, by performing measurement using the reflection characteristic measurement apparatus 1A in a state where the color patch sheet 71 insertable through the gap 99 is inserted through the gap 99 with the color patch sheet 71 defined as the measurement target, it is possible to reduce the difference between the white calibration distance D1 and the measurement distance D2.

The white calibration plate 31 may be provided to allow its measurement surface 32 to be substantially flush with a main surface facing the support part 51E, among the main surface of the facing part 56E.

6. Sixth Embodiment

Figure 13:
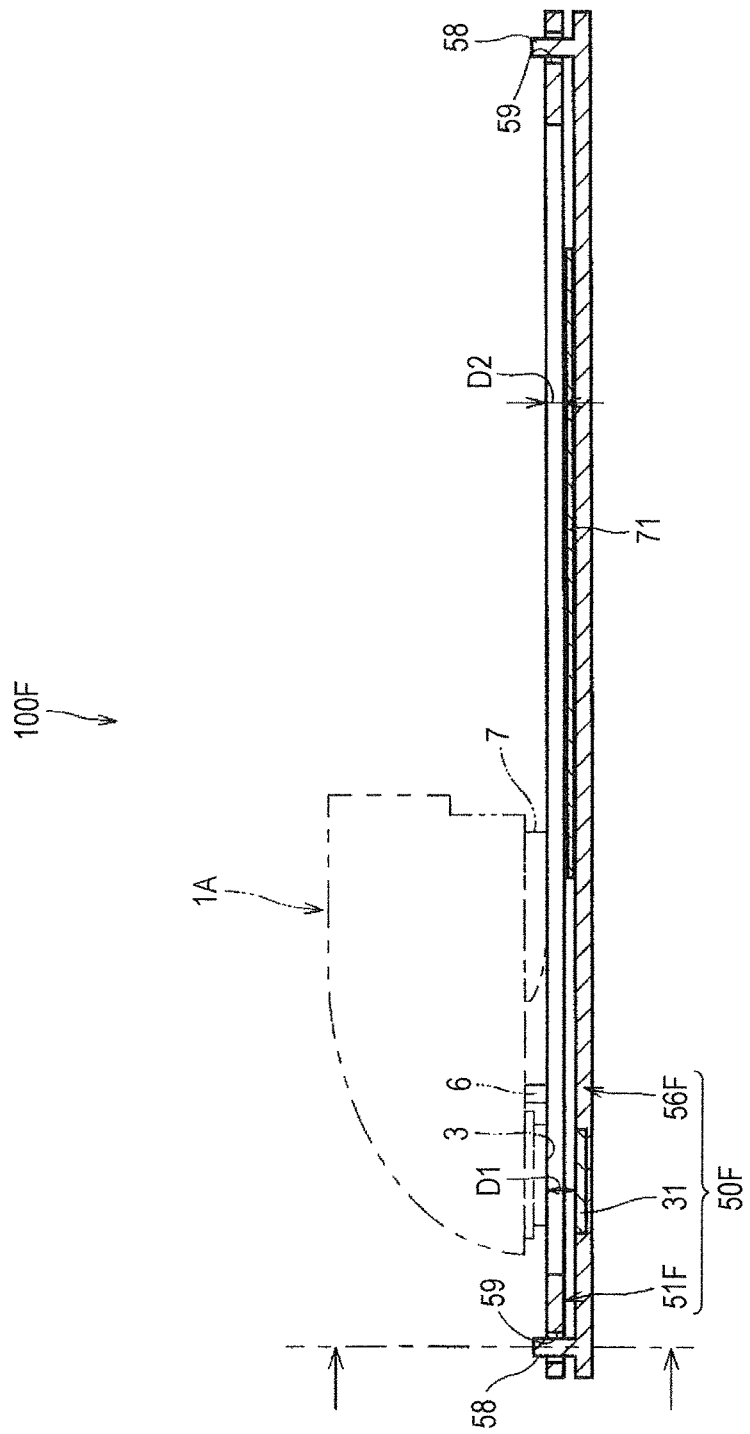
FIG. 13 is a schematic side sectional view illustrating a configuration of a reflection characteristic measurement system according to a sixth embodiment.
Figure 14:
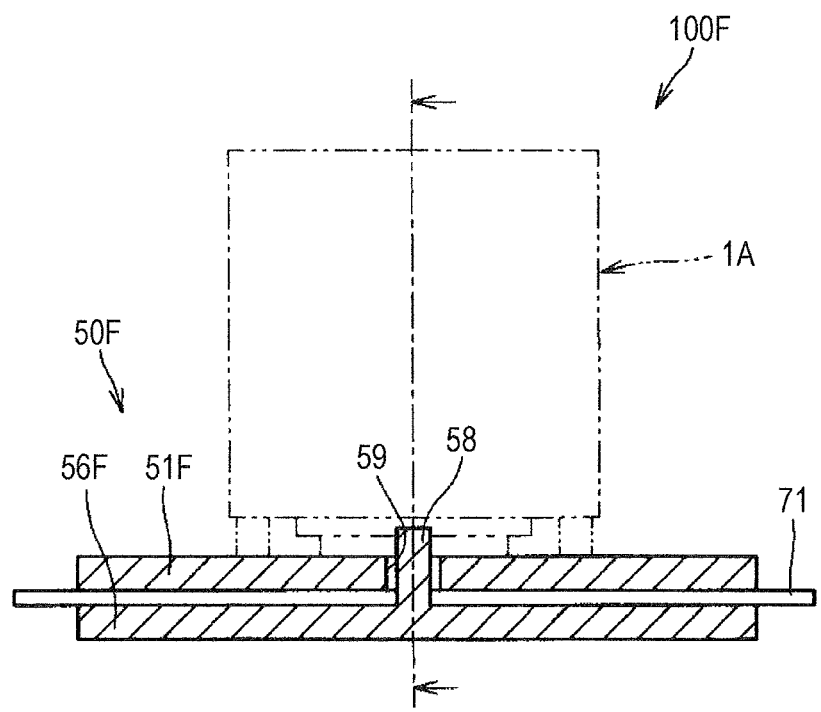
FIG. 14 is a schematic front sectional view of the reflection characteristic measurement system of FIG. 13.

FIG. 13 is a schematic side sectional view illustrating a configuration of a reflection characteristic measurement system 100F according to a sixth embodiment. FIG. 14 is a schematic front sectional view of the reflection characteristic measurement system 100F.

As illustrated in FIGS. 13 and 14, the reflection characteristic measurement system 100F is configured similarly to the reflection characteristic measurement system 100A except that a guide member 50F is provided in place of the guide member 50A of the reflection characteristic measurement system 100A. The guide member 50F is configured similarly to the guide member 50A, except that the guide member 50F includes a support part 51F in place of the support part 51A of the guide member 50A, and further includes a facing part 56F.

The support part 51F is a plate-shaped part for supporting the reflection characteristic measurement apparatus 1A. The facing part 56F is a plate-shaped part that faces the support part 51F and includes the white calibration plate 31 and formed separately from the support part 51F.

A projecting piece 58 projects from a main surface facing the support part 51F, among the two main surfaces of the facing part 56F. At a part of the support part 51F that faces the projecting piece 58, there is provided a through hole 59 having a diameter larger than a diameter of the projecting piece 58 and capable of inserting the projecting piece 58 up to the proximal end part of the projecting piece 58. The support part 51F is configured similarly to the support part 51A except that the white calibration plate 31 is not provided and that the through hole 59 is provided in each of parts in the vicinity of both ends.

With this configuration of the reflection characteristic measurement system 100F, it is possible to perform scan measurement of the white calibration plate 31 and the color patch sheet 71 with the color patch sheet 71 being sandwiched between the support part 51F and the facing part 56F. This measurement enables reduction of the difference between the white calibration distance D1 and the measurement distance D2.

The white calibration plate 31 may be provided to allow its measurement surface 32 to be substantially flush with a main surface facing the support part 51F, among the main surface of the facing part 56F.

While the example of FIG. 13 is a case where the two projecting pieces 58 are provided in the vicinity of both ends of the facing part 56F in the longitudinal direction of the elongated hole 52, it is allowable to arrange one projecting piece 58 in the vicinity of one end of the facing part 56F. In this case, in order to suppress the relative rotation of the support part 51F and the facing part 56F with the projecting piece 58 as the rotation axis, it is preferable to employ the projecting piece 58 and the through hole 59 each having a shape elongated in a direction parallel to the support surface of the support part 51F and transverse to the longitudinal direction of the elongated hole 52.

While the example of FIG. 13 is a case where the projecting piece 58 penetrates through the through hole 59, the projecting piece 58 may be shorter than the axial length of the through hole 59. In this case, the distal end of the projecting piece 58 does not penetrate through the through hole 59 even when the projecting piece 58 is accommodated in the through hole 59 up to the proximal end part of the piece. In this case, instead of the through hole 59, it is allowable to provide in the support part 51F an accommodating hole having a length capable of accommodating the projecting piece 58 up to the proximal end part and that would not penetrate through the support part 51F because of its size that is shorter than the thickness of the support part 51F.

Furthermore, the accommodating hole may be provided in the facing part 56F rather than the support part 51F, and the projecting piece 58 may be provided in the support part 51F rather than the facing part 56F. In this case, the accommodating hole opens on an upper surface of the facing part 56F to extend toward a lower surface side, and the projecting piece 58 projects from the lower surface of the support part 51F toward the facing part 56F side.

Accordingly, as described above, in the guide member 50F of the reflection characteristic measurement system 100F, the projecting piece 58 projects from the side of one of the support part 51F and the facing part 56F toward the other side. At a part of the other side that faces the projecting piece 58, there is provided a hole having a larger diameter than the diameter of the projecting piece 58 and capable of inserting (accommodating) the projecting piece 58 to the proximal end part of the projecting piece 58.

With the reflection characteristic measurement system according to any of the first to sixth embodiments configured as described above, the reflection characteristic measurement apparatus is guided and moved by the guide groove 53 formed in the support part of the guide member to move the light receiving opening 3 of the reflection characteristic measurement apparatus along the moving path 97, and the moving path 97 extends in one direction including a path in which the light receiving opening 3 moves while facing the elongated hole 52 extending in the one direction. The white calibration plate 31 is provided above the moving path 97 of the light receiving opening 3 in plan view of the support part such that the light receiving opening 3 faces the measurement surface 32 of the white calibration plate 31 when the light receiving opening 3 moves along a part of the moving path 97. With this configuration, the reflection characteristic measurement apparatus can perform measurement for white calibration and measurement of the color patch sheet 71 in a process in which the reflection characteristic measurement apparatus is guided and moved by the guide groove 53. This configuration can omit measure's operation of removing the reflection characteristic measurement apparatus from the guide member during a period between the measurement for white calibration and the measurement of the color patch sheet 71, leading to the reduction of the burden on the measurer at the time of white calibration.

Moreover, with the reflection characteristic measurement system according to any of the first to sixth embodiments, the measurement controller of the reflection characteristic measurement apparatus causes the reflection characteristic measurement apparatus to perform the measurement for white calibration a predetermined number of times necessary for white calibration by distributing the measurement to each of a plurality of time of input periods of the measurement signal. This makes it possible to reduce the number of times of measurement for white calibration during one measurement signal input period than the predetermined number of times needed for white calibration. This leads to reduction of the measurement time for white calibration in a case where measurement of the color patch sheet 71 is performed for a plurality of times.

Moreover, with the reflection characteristic measurement system according to any of the first to sixth embodiments, the measurement controller selectively performs the first control of controlling the reflection characteristic measurement apparatus to perform measurement for white calibration a predetermined number of times necessary for white calibration within one input period of the measurement signal, and the second control of controlling the reflection characteristic measurement apparatus to perform a predetermined number of times of white calibration measurements by distributing the measurement to each of a plurality of number of times of input periods of the measurement signal. This makes it possible to reduce the number of times of measurement for white calibration during one measurement signal input period by the second control than by the first control. This leads to reduction of the measurement time for white calibration with the second control by a measurement controller in a case where measurement of the color patch sheet 71 is performed for a plurality of times.

Moreover, according to the reflection characteristic measurement system of the first embodiment, the white calibration plate 31 is provided on the guide member such that the white calibration distance D1 differs from the measurement distance D2, and the calculator of the reflection characteristic measurement apparatus calculates the reflectance Rm($\lambda$) such that the reflectance Rm($\lambda$) of the color patch sheet 71 in which the distance from the light receiving opening 3 is the measurement distance D2 satisfies Formula (1). Accordingly, the reflectance of the color patch sheet 71 can be calculated with a feedback of a difference between D white calibration distance D1 and the measurement distance D2, making it possible to enhance the accuracy of the calculation.

Moreover, according to the reflection characteristic measurement system of the third embodiment, the first thickness D3 of the support part 51C of the guide member 50C and the second thickness D4 of the support part 51C of the guide member 50C are different from each other to equalize the white calibration distance D1 and the measurement distance D2. With this configuration, the white calibration distance D1 and the measurement distance D2 are equalized even when the measurement surface 32 of the white calibration plate 31 and the measurement surface 72 of the color patch sheet 71 are not on a same plane, making it possible to enhance the calculation accuracy of the reflectance of the patch sheet 71.

Moreover, according to the reflection characteristic measurement system of the fifth embodiment, the connecting part 57 connects the support part 51E with the facing part 56E so as to allow the support part 51E and the facing part 56E to face each other with respect to the guide member 50E across the predetermined gap 99 extending in one direction. With this configuration, in a case where the color patch sheet 71 insertable through the gap 99 between the support part 51E and the facing part 56F is measured while being inserted in the gap 99, it is possible to arrange the main surface (lower surface) on an opposite side to a measurement surface 32 among both main surfaces of the white calibration plate 31 at a position farther than the color patch sheet 71, with respect to the light receiving opening 3. This makes it possible to reduce the difference in the distances of the white calibration plate 31 and the color patch sheet 71, toward the light receiving opening 3.

According to the reflection characteristic measurement system of the sixth embodiment, the guide member 50F faces the support part 51F, and includes a white calibration plate 31, and is formed as a plate-shaped member formed separately from the support part 51F And a facing part 56F. The projecting piece 58 projects from one main surface of the support part 51F and the facing part 56F toward the other, and the part of the other of the support part 51F and the facing part 56 facing the projecting piece 58 includes a hole with a diameter larger than the projecting piece 58 and capable of accommodating the projecting piece 58 up to the proximal end part of the projecting piece 58. This makes it possible to perform measurement with the color patch sheet 71 sandwiched between the facing part 56F and the support part 51E This allows the main surface on the opposite side of the measurement surface 32 among both main surfaces of the white calibration plate 31 to be arranged farther than the color patch sheet 71, with respect to the light receiving opening 3. This makes it possible to reduce the difference in the distances of the white calibration plate 31 and the color patch sheet 71, toward the light receiving opening 3.

Moreover, with the reflection characteristic measurement system according to the second embodiment, the white calibration plate 31 is provided at a part on one end side in one direction (extension direction of the elongated hole 52) of the guide member 50B, and the support part 51B includes the abutment part 83 protruding from the part of the support surface 54 on the one end side of the guide member 50B, and the abutment part 83 is provided on the support part 51B such that the abutment part 83 abuts the reflection characteristic measurement apparatus in a state where the light receiving opening 3 faces a predetermined part on the one end side of the measurement surface 32 of the white calibration plate 31 to enable regulation of the movement of the reflection characteristic measurement apparatus to the one end side. This makes it possible to facilitate starting movement of the reflection characteristic measurement apparatus from a predetermined part of the white calibration plate 31 by allowing the reflection characteristic measurement apparatus to abut the abutment part 83.

Moreover, with the reflection characteristic measurement system according to any of the first to third embodiments and fifth to sixth embodiments, the determiner 29 determines whether the light receiving opening 3 faces the white calibration plate 31 on the basis of the intensity of the light received by the light receiving opening 3 of the reflection characteristic measurement apparatus. This makes it possible to determine whether the light receiving opening 3 faces the white calibration plate 31 without separately providing a sensor for the determination.

Moreover, according to the reflection characteristic measurement system of the fourth embodiment, the positional relationship of the projection 55 with respect to the white calibration plate 31 in one direction, that is, the extending direction of the elongated hole 52, is substantially equal to the positional relationship of the sensor 8 with respect to the light receiving opening 3 of the reflection characteristic measurement apparatus supported by the support part 51D. Accordingly, by detecting the projection 55 by the sensor 8, it is possible to detect that the light receiving opening 3 faces the white calibration plate 31.

Moreover, with the reflection characteristic measurement system according to any of the first to sixth embodiments, the measurement surface 32 of the white calibration plate 31 is longer in one direction along the measurement surface 32, that is, longer in the one direction than in a direction crossing the extending direction of the elongated hole 52. This configuration facilitates increasing the number of measurement positions on the measurement surface 32 of the white calibration plate 31, making it possible to enhance the reliability of white calibration.

Moreover, with the reflection characteristic measurement system according to any of the first to sixth embodiments, a failure in acquisition of a predetermined number of measurement values available for white calibration as a result of measurement for white calibration by the reflection characteristic measurement apparatus, this failure is notified by a warning issued by a warning part. This enhances the reliability of the calculated reflectance of the color patch sheet 71.

Although embodiments of the present invention have been described and illustrated in detail, the disclosed embodiments are made for purposes of illustration and example only and not limitation. The scope of the present invention should be interpreted by terms of the appended claims. Accordingly, the present invention can appropriately modify and omit the embodiment within the scope of the invention.

What is claimed is:

1. A reflection characteristic measurement system comprising:
a hand-held reflection characteristic measurement apparatus including, on a bottom part, a light receiver that receives reflected light obtained by emitting illumination light to a measurement target; and
a guide member that supports the reflection characteristic measurement apparatus in a state of covering the measurement target so as to allow the light receiver to face the measurement target,
wherein the guide member includes:
a plate-shaped support part having a support surface to support the reflection characteristic measurement apparatus so as to enable the reflection characteristic measurement apparatus to move; and
a white calibration plate provided on the guide member and applicable to white calibration of the reflection characteristic measurement apparatus,
the support part includes:
an elongated hole extending in one direction along the support surface to penetrate through the support part; and
a guide structure provided to guide the reflection characteristic measurement apparatus so as to enable the apparatus to move along the one direction while being supported by the supporting surface,
the light receiver is provided on the reflection characteristic measurement apparatus so as to move along a predetermined moving path by movement of the reflection characteristic measurement apparatus guided by the guide structure,
the moving path of the light receiver extends in the one direction including a path of the light receiver to move in the one direction while facing the elongated hole, and
the white calibration plate is provided on the moving path in plan view of the support part such that the light receiver faces a measurement surface of the white calibration plate when the light receiver moves along a part of the moving path.

2. The reflection characteristic measurement system according to claim 1,
wherein the reflection characteristic measurement apparatus further includes a hardware processor that detects a predetermined measurement signal input to the reflection characteristic measurement apparatus and causes the reflection characteristic measurement apparatus to perform measurement for the white calibration and measurement for the measurement target, and
the hardware processor controls the reflection characteristic measurement apparatus to perform the measurement for white calibration of a predetermined number of times necessary for the white calibration by distributing the measurement to each of a plurality of number of times of input periods of the measurement signal.

3. The reflection characteristic measurement system according to claim 1,
wherein the hardware processor detects a predetermined measurement signal input to the reflection characteristic measurement apparatus and causes the reflection characteristic measurement apparatus to perform measurement for the white calibration and measurement for the measurement target, and
the hardware processor selectively performs first control of controlling the reflection characteristic measurement apparatus to perform measurement for white calibration a predetermined number of times necessary for white calibration within one input period of the measurement signal, and second control of controlling the reflection characteristic measurement apparatus to perform a predetermined number of white calibration measurements by distributing the measurement to each of a plurality of number of times of input periods of the measurement signal.

4. The reflection characteristic measurement system according to claim 1,
wherein
when a white calibration distance is defined by a distance from the light receiver of the reflection characteristic measurement apparatus supported by the support part of the guide member to the white calibration plate, and
when a measurement distance is defined by a distance from the light receiver of the reflection characteristic measurement apparatus supported by the support part of the guide member to the measurement target facing the elongated hole while being covered by the guide member,
the white calibration plate is provided on the guide member such that the white calibration distance and the measurement distance differ from each other, and
the hardware processor calculates a reflectance of the measurement target in which a distance from the light receiver is the measurement distance, so as to satisfy Formula (I):

[Mathematical Formula 1]

$$Rm(\lambda) = Rw0(\lambda) \times Im(\lambda)/Iwc1(\lambda) \times Iwc2(\lambda)/Iwc3(\lambda) \quad (I)$$

where
$Rm(\lambda)$ represents spectral reflectance of the measurement target, in which the distance from the light receiving opening is the measurement distance,
$Rw0(\lambda)$ represents valued spectral reflectance of the white calibration plate in which the distance from the light receiving opening is the measurement distance,
$Im(\lambda)$ represents reflected light intensity obtained by the reflection characteristic measurement apparatus by measurement of the reflected light from the white calibration plate in which the distance from the light receiving opening is the measurement distance,
$Iwc1(\lambda)$ represents reflected light intensity obtained by the reflection characteristic measurement apparatus by measurement of the reflected light from the white calibration plate in which the distance from the light receiving opening is the white calibration distance,
$Iwc2(\lambda)$ represents reflected light intensity preliminarily obtained by the reflection characteristic measurement apparatus by measurement of the reflected light from the white calibration plate in which the distance from the light receiving opening is the white calibration distance, and
$Iwc3(\lambda)$ represents reflected light intensity obtained at the measurement of $Iwc2(\lambda)$ by the reflection characteristic measurement apparatus by measurement of the reflected light from the white calibration plate in which the distance from the light receiving opening is the measurement distance.

5. The reflection characteristic measurement system according to claim 1,
wherein
when a white calibration distance is defined by a distance from the light receiver of the reflection characteristic measurement apparatus supported by the support part of the guide member to the white calibration plate,
when a measurement distance is defined by a distance from the light receiver of the reflection characteristic measurement apparatus supported by the support part of the guide member to the measurement target facing the elongated hole while being covered by the guide member,
when a first thickness is defined by a part to support the reflection characteristic measurement apparatus so as to allow the light receiver to face the white calibration plate, among the support part of the guide member, and
when a second thickness is defined by a part to support the reflection characteristic measurement apparatus so as to allow the light receiver to face the measurement target, among the support part,
the first thickness and the second thickness differ from each other so as to equalize the white calibration distance and the measurement distance.

6. The reflection characteristic measurement system according to claim 1,
wherein the guide member includes:
a plate-shaped facing part facing the support part and having the white calibration plate; and
a connecting part that connects the support part and the facing part so as to allow the support part and the facing part to face each other across a predetermined gap extending in the one direction, and
a width of the gap in a direction penetrating the support surface is wider than a thickness of the measurement target in the direction, and a length of the gap in the one direction is longer than a length of the measurement target in the one direction.

7. The reflection characteristic measurement system according to claim 1,
wherein the guide member further includes a plate-shaped facing part facing the support part, including the white calibration plate, and being formed separately from the support part,
a projecting piece projects from one main surface of the support part and the facing part toward the other, and
a part of the other of the support part and the facing part, facing the projecting piece includes a hole having a diameter larger than a diameter of the projecting piece and capable of accommodating the projecting piece up to a proximal end part of the projecting piece.

8. The reflection characteristic measurement system according to claim 1,
wherein the white calibration plate is provided at a part on one end side in one direction of the guide member,
the support part includes an abutment part protruding from the part of the support surface on the one end side of the guide member, and
the abutment part is provided on the support part such that the abutment part abuts the reflection characteristic measurement apparatus in a state where the light receiver faces a predetermined part of the measurement surface of the white calibration plate to enable regulation of the movement of the reflection characteristic measurement apparatus to the one end side.

9. The reflection characteristic measurement system according to claim 1,
wherein the hardware processor determines whether the light receiver of the reflection characteristic measurement apparatus faces the white calibration plate.

10. The reflection characteristic measurement system according to claim 9,
wherein the hardware processor determines whether the light receiver of the reflection characteristic measurement apparatus faces the white calibration plate on the basis of intensity of light received by the light receiver of the reflection characteristic measurement apparatus.

11. The reflection characteristic measurement system according to claim 9,
wherein the guide member further includes an identification mark provided on a movement trajectory of the support part in plan view with respect to the movement trajectory of the reflectance characteristic measurement apparatus supported by the support part and guided and moved by the guide structure and having substantially a same length as a length of the white calibration plate in the one direction,
the reflection characteristic measurement apparatus further include/es a sensor that detects the identification mark and outputs a detection signal,
a positional relationship of the identification mark with respect to the white calibration plate in the one direction is substantially equal to a positional relationship of the sensor with respect to the light receiver of the reflection characteristic measurement apparatus supported by the support part in the one direction in the one direction, and
the hardware processor determines whether the light receiver faces the white calibration plate on the basis of the detection signal.

12. The reflection characteristic measurement system according to claim 1,
wherein the measurement surface of the white calibration plate is longer in the one direction than in a direction crossing the one direction along the measurement surface.

13. The reflection characteristic measurement system according to claim 1,
wherein the hardware processor issues a warning in a case where a predetermined number of measurement values available for the white calibration cannot be obtained as a result of the measurement for white calibration.

* * * * *